(12) United States Patent
Frudakis

(10) Patent No.: US 7,107,155 B2
(45) Date of Patent: Sep. 12, 2006

(54) METHODS FOR THE IDENTIFICATION OF GENETIC FEATURES FOR COMPLEX GENETICS CLASSIFIERS

(75) Inventor: Tony Nick Frudakis, Bradenton, FL (US)

(73) Assignee: DNAPrint Genomics, Inc., Sarasota, FL (US)

( * ) Notice: Subject to any disclaimer, the term of this patent is extended or adjusted under 35 U.S.C. 154(b) by 490 days.

(21) Appl. No.: 10/120,804

(22) Filed: Apr. 11, 2002

(65) Prior Publication Data

US 2003/0171878 A1 Sep. 11, 2003

Related U.S. Application Data

(60) Provisional application No. 60/338,771, filed on Dec. 3, 2001.

(51) Int. Cl.
*G06F 19/00* (2006.01)
*G11C 17/00* (2006.01)
*G05B 15/00* (2006.01)

(52) U.S. Cl. ............................. 702/19; 365/94; 700/1
(58) Field of Classification Search ................ 702/19; 365/94; 700/1
See application file for complete search history.

(56) References Cited

U.S. PATENT DOCUMENTS

| | | | |
|---|---|---|---|
| 5,541,067 | A | 7/1996 | Perlin |
| 6,291,182 | B1 | 9/2001 | Schork et al. |

FOREIGN PATENT DOCUMENTS

| | | |
|---|---|---|
| WO | WO 01/01218 A2 | 1/2001 |
| WO | WO 02/20835 A2 | 3/2002 |
| WO | WO 02/31188 A2 | 4/2002 |
| WO | WO 02/35442 A2 | 5/2002 |
| WO | WO 03/016565 | 2/2003 |

OTHER PUBLICATIONS

Martin et al. SNPing Away at Complex Diseases: Analysis of Single-Nucleotide Polymorphisms around APOE in Alzheimer Disease. Am. J. Hum. Genet. vol. 67, pp. 383-394 (2000).*

Malhotra et al. The dopamine D3 receptor (DRD3) Ser9Gly polymprphism and schizophrenia: a haplotype relative risk study and association with clozapine response. Molecular Psychiatry vol. 3, pp. 72-75 (1998).*

Weintrob N et al, Type 1 diabetes environmental factors and correspondence analysis of HLA class II genes in the Yemenite Jewish Community in Israel, Diabetes Care 2001 United States, vol. 24, No. 4, Apr. 2001, pp. 650-653.

Mayer S, et al., "Haplotype Study of the HLA-A,B,C and Bf Associations by the Factorial Correspondence Analysis", Journal of Immungenetics, vol. 8, No. 1, 1981, pp. 7-14.

M.J. Greenacre, L. Degos: "Correspondence Analysis of HLA Gene Frequency Data from 124 Population Samples", American Society of Human Genetics, 1977, pp. 60-75.

Lucek Paul et al., "Multi-locus nonparametric linkage analysis of complex trait loci with neural networks", Human Heredity, vol. 48, No. 5, Sep. 1998, pp. 275-284.

Fellenberg Kurt et al., "Correspondence analysis applied to microarray data", Proceedings of the National Academy of Sciences of the United States, vol. 98, No. 19, Sep. 11, 2001, pp. 10781-10786.

Tertwilliger J D et al., "Gene mapping in the 20th and 21st centuries: statistical methods, data analysis and experimental design" Human Biology, XX XX, vol. 72, No. 1, Bebruary 2000 (200-02), pp. 63-132.

Lander and Kruglyak, "Genetic Dissection of Complex Traits: Guidelines For Interpreting and Reporting Linkage Results", Nature Genetics, New York, NY, US, vol. 11, Nov. 1995, pp. 241-247.

J.S. Palmer et al., "Melanocortin-1 Receptor Polymorphisms and Risk of Melanoma: Is the Association Explained Soley by Pigmentation Phenotype?", AM> J. Hum. Genet., vol. 66, 2000, pp. 176-186.

PCT International Application No. PCT/US02/38309; Frudakis; Entitled "Methods and Apparatus for Use in Genetics Classification Including Classification Tree Analysis".

PCT International Application No. PCT/US02/41465; Frudakis et al.; Entitled "Methods and Apparatus for Complex Genetics Classification Based on Correspondence Analysis and Linear/Quadratic Analysis".

* cited by examiner

*Primary Examiner*—John S. Brusca
(74) *Attorney, Agent, or Firm*—John J. Oskorep, Esq.

(57) ABSTRACT

A candidate single nucleotide polymorphism (SNP) combination is selected from a plurality of candidate SNP combinations for a gene associated with a genetic trait. Haplotype data associated with this candidate SNP combination are read for a plurality of individuals and grouped into a positive-responding group and a negative-responding group based on whether a predetermined trait criteria for an individual is met. A statistical analysis on the grouped haplotype data is performed to obtain a statistical measurement. The acts of selecting, reading, grouping, and performing are repeated as necessary to identity the candidate SNP combination having the optimal statistical measurement. In one approach, a directed search based on results of previous statistical analysis of SNP combinations is performed until the optimal statistical measurement is obtained. In addition, the number of SNP combinations selected and analyzed may be reduced based on a simultaneous testing procedure.

21 Claims, 20 Drawing Sheets

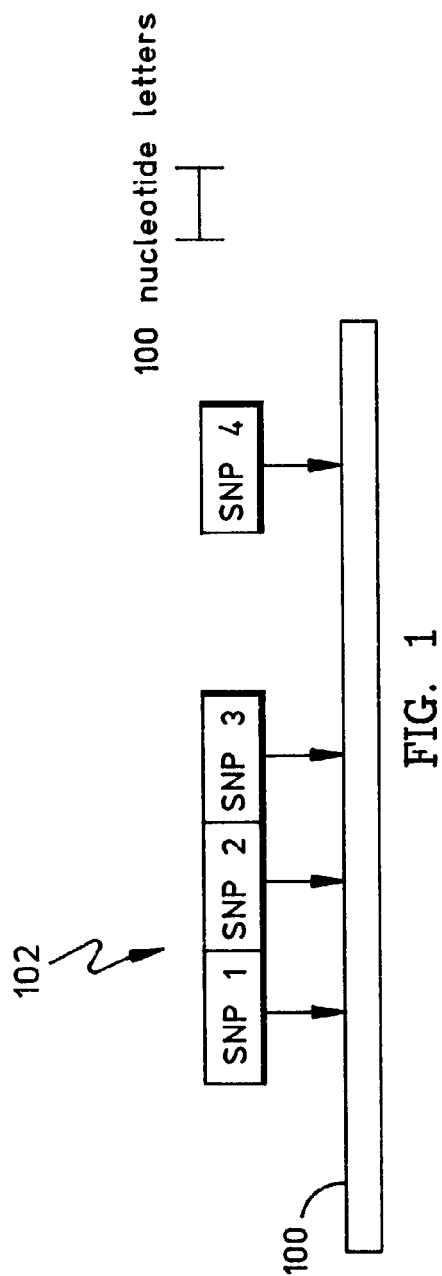

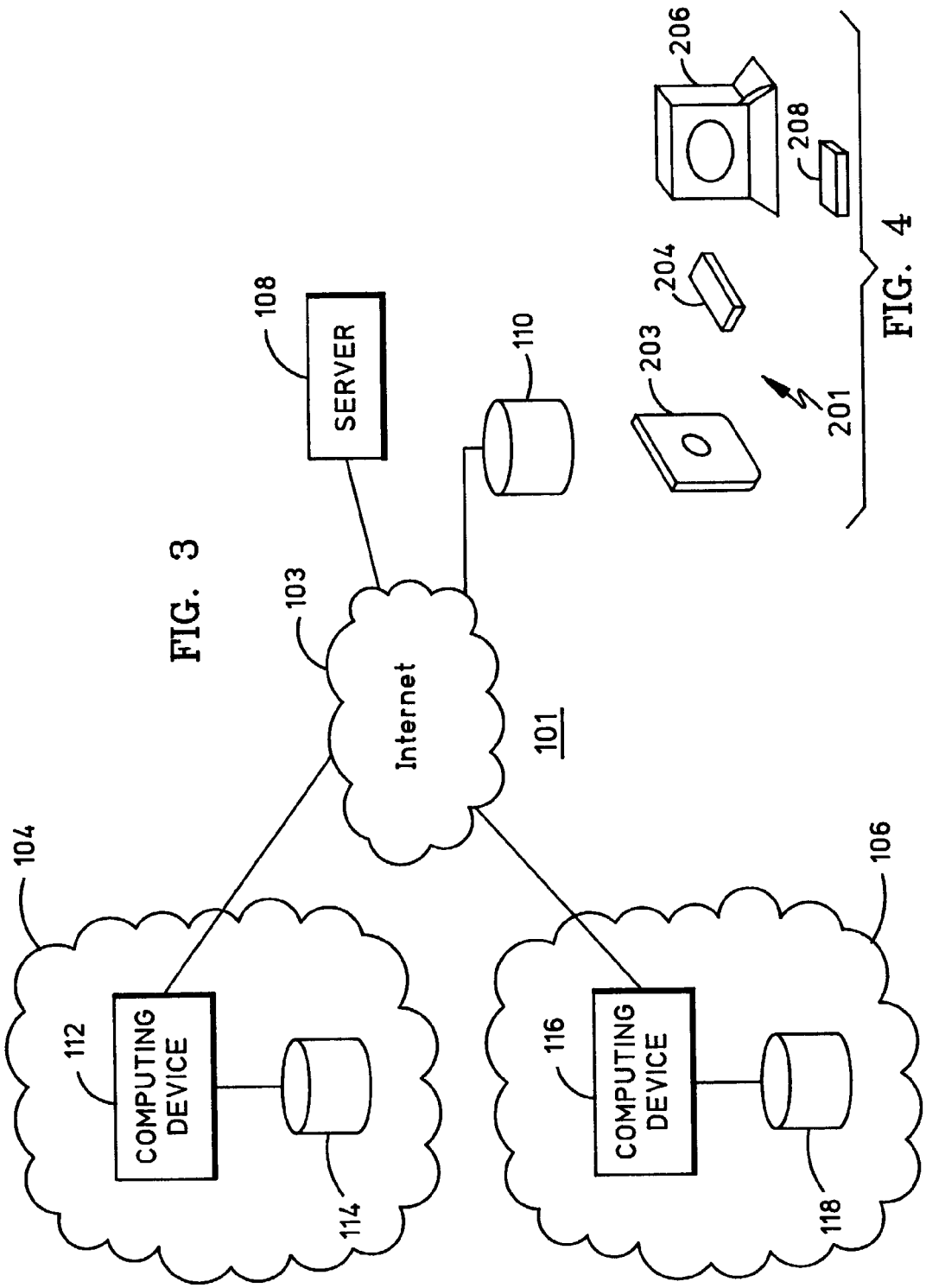

| SNPNAME | MARKER | LOCATION | GENBANK | INTEGRITY | TYPE |
|---|---|---|---|---|---|
| CYP3A4E3-5_249 | 809114 | 5230 | AF209389 | POLY | INTRON |
| CYP3A4E7_117 | 664802 | 13684 | AF209389 | POLY | SILENT |
| CYP3A4E7_243 | 664803 | 14889 | AF209389 | POLY | INTRON |
| CYP3A4E8E9-5_460 | 809121 | 17998 | AF209389 | POLY | INTRON |
| CYP3A4E10-5_292 | 712037 | 21892 | AF209389 | POLY | INTRON |
| CYP3A4E11-5_242 | 809111 | 21900 | AF209389 | POLY_RARE | SILENT |
| CYP3A4E12_9 | 869771 | 22201 | AF209389 | POLY_RARE | INTRON |
| CYP3A4E12_76 | 869772 | 24323 | AF209389 | POLY | INTRON |

FIG. 8

```
[[Samples]]
    SampleName="RESPONDERS"
    SampleSize= 37
    SampleData={
    H1      10      A T G C
                    A T A C
    H2      25      A T G C
                    A T G C
    H3      1       A G A C
                    A T G C
    H4      1       A G A C
                    A T A C
    }
    SampleName="NON-RESPONDERS"
    SampleSize= 106
    SampleData={
    H1      16      A G A C
                    A T G C
    H2      12      A T G C
                    A T A C
    H3      62      A T G C
                    A T G C
    H4      4       A G A T
                    A G G C
    H5      7       A T G C
                    A G A T
    H6      1       A t A C
                    A g A T
    H7      4       A G A C
                    A T A C
    }
```

FIG. 11

Gene: CYP3A-4
Marker: 664803

| SAMPLE ID | DRUG | START DATE | STOP DATE | TEST | TEST DATE (BEFORE) / TEST DATE (AFTER) | READING | 809114 | 664803 | 712037 | 869772 | HAIR | EYE |
|---|---|---|---|---|---|---|---|---|---|---|---|---|
| DNAP00118 | TAXOL | 2000-05-03 | null | CA125 | 2000-05-03 | 50.2 | AA | GT | GA | CC | brown | brown1 |
| | | | | | 2000-06-01 | 47.2 | | | | | | |
| DNAP00118 | TAXOL | 2000-06-01 | null | CA125 | 2000-06-01 | 47.2 | AA | GT | GA | CC | brown | brown1 |
| | | | | | 2000-06-22 | 53 | | | | | | |
| DNAP00118 | TAXOL | 2000-06-22 | null | CA125 | 2000-06-22 | 53 | AA | GT | GA | CC | brown | brown1 |
| | | | | | 2000-07-11 | 55 | | | | | | |
| DNAP00118 | TAXOL | 2000-11-02 | null | CA125 | 2000-10-26 | 53 | AA | GT | GA | CC | brown | brown1 |
| | | | | | 2000-11-21 | 58 | | | | | | |
| DNAP00118 | TAXOL | 2000-10-03 | null | CA125 | 2000-10-03 | 44 | AA | GT | GA | CC | brown | brown1 |
| | | | | | 2000-10-26 | 53 | | | | | | |
| DNAP00118 | TAXOL | 2000-08-03 | null | CA125 | 2000-08-01 | 62 | AA | GT | GA | CC | brown | brown1 |
| | | | | | 2000-08-19 | 53 | | | | | | |

| | | | | | | | | | |
|---|---|---|---|---|---|---|---|---|---|
| DNAP00118 | TAXOL | 2000-07-13 | null | CA125 | 2000-07-11 | 55 | AA | GT | GA | CC | brown | brown1 |
| DNAP00119 | TAXOL | 2000-10-20 | null | CA125 | 2000-08-01 | 62 | | | | | | |
| DNAP00119 | TAXOL | 2000-12-29 | null | CA125 | 2000-10-19 | 1064.2 | AA | TT | GA | CC | black | black |
| DNAP00119 | TAXOL | 2000-12-04 | null | CA125 | 2000-11-09 | 207.7 | | | | | | |
| DNAP00119 | TAXOL | 2000-10-23 | null | CA125 | 2000-12-27 | 20 | AA | TT | GA | CC | black | black |
| DNAP00119 | TAXOL | 2000-11-13 | null | CA125 | 2001-01-17 | 14.3 | | | | | | |
| DNAP00119 | TAXOL | 2000-10-16 | null | CA125 | 2000-12-01 | 93.9 | AA | TT | GA | CC | black | black |
| | | | | | 2000-10-19 | 1064.2 | AA | TT | GA | CC | black | black |
| | | | | | 2000-12-27 | 20 | | | | | | |
| | | | | | 2000-11-09 | 207.7 | AA | TT | GA | CC | black | black |
| | | | | | 2000-12-01 | 93.9 | | | | | | |
| DNAP00120 | | | | | 2000-10-04 | 74 | AA | TT | GA | CC | black | brown1 |
| | | | | | 2000-11-17 | 6 | | | | | | |

FIG. 9B

Marker: 712037

| SAMPLE ID | DRUG | START DATE | STOP DATE | TEST | TEST DATE (BEFORE) | TEST DATE (AFTER) | READING | 809114 | 664803 | 712037 | 869772 | HAIR | EYE |
|---|---|---|---|---|---|---|---|---|---|---|---|---|---|
| DNAP00118 | TAXOL | 2000-05-03 | null | CA125 | 2000-05-03 | | 50.2 | AA | GT | GA | CC | brown | brown1 |
| | | | | | | 2000-06-01 | 47.2 | | | | | | |
| DNAP00118 | TAXOL | 2000-06-01 | null | CA125 | 2000-06-01 | | 47.2 | AA | GT | GA | CC | brown | brown1 |
| | | | | | | 2000-06-22 | 53 | | | | | | |
| DNAP00118 | TAXOL | 2000-06-22 | null | CA125 | 2000-06-22 | | 53 | AA | GT | GA | CC | brown | brown1 |
| | | | | | | 2000-07-11 | 55 | | | | | | |
| DNAP00118 | TAXOL | 2000-11-02 | null | CA125 | 2000-10-26 | | 53 | AA | GT | GA | CC | brown | brown1 |
| | | | | | | 2000-11-21 | 58 | | | | | | |
| DNAP00118 | TAXOL | 2000-10-03 | null | CA125 | 2000-10-03 | | 44 | AA | GT | GA | CC | brown | brown1 |
| | | | | | | 2000-10-26 | 53 | | | | | | |
| DNAP00118 | TAXOL | 2000-08-03 | null | CA125 | 2000-08-01 | | 62 | AA | GT | GA | CC | brown | brown1 |
| | | | | | | 2000-08-19 | 53 | | | | | | |

FIG. 9C

| DNAP00118 | TAXOL | 2000-07-13 | null | CA125 | 2000-07-11 | 55 | AA | GT | GA | CC | brown | brown1 |
| DNAP00118 | TAXOL | 2000-10-20 | null | | | | | | | | | |
| | | | | | 2000-08-11 | 62 | | | | | | |
| DNAP00118 | TAXOL | 2000-12-29 | null | CA125 | 2000-10-19 | 1064.2 | AA | TT | GA | CC | black | black |
| | | | | | 2000-11-09 | 207.7 | | | | | | |
| DNAP00118 | TAXOL | 2000-12-04 | null | CA125 | 2000-12-27 | 20 | AA | TT | GA | CC | black | black |
| | | | | | 2001-01-17 | 14.3 | | | | | | |
| DNAP00118 | TAXOL | 2000-10-23 | null | CA125 | 2000-12-01 | 93.9 | AA | TT | GA | CC | black | black |
| | | | | | 2000-12-27 | 20 | | | | | | |
| DNAP00118 | TAXOL | 2000-11-13 | null | CA125 | 2000-10-19 | 1064.2 | AA | TT | GA | CC | black | black |
| | | | | | 2000-11-09 | 207.7 | | | | | | |
| DNAP00118 | TAXOL | 2000-10-04 | null | CA125 | 2000-11-09 | 207.7 | AA | TT | GA | CC | black | black |
| | | | | | 2000-12-01 | 93.9 | | | | | | |
| DNAP00118 | TAXOL | 2000-10-16 | null | CA125 | 2000-10-04 | 74 | AA | TT | GA | CC | black | brown1 |
| | | | | | 2000-11-17 | 6 | | | | | | |

FIG. 9D

Gene: CYP3A-4
Marker: 664803

| SAMPLE ID | DRUG | START DATE | STOP DATE | TEST | TEST DATE (BEFORE) / TEST DATE (AFTER) | READING | 80911466480371203786972 | HAIR | EYE |
|---|---|---|---|---|---|---|---|---|---|
| DNAP00118 | TAXOL | 2000-05-03 | null | CA125 | 2000-05-03 | 50.2 | AGAC/ATGC | brown | brown1 |
|  |  |  |  |  | 2000-06-01 | 47.2 |  |  |  |
| DNAP00118 | TAXOL | 2000-06-01 | null | CA125 | 2000-06-01 | 47.2 | AGAC/ATGC | brown | brown1 |
|  |  |  |  |  | 2000-06-22 | 53 |  |  |  |
| DNAP00118 | TAXOL | 2000-06-22 | null | CA125 | 2000-06-22 | 53 | AGAC/ATGC | brown | brown1 |
|  |  |  |  |  | 2000-07-11 | 55 |  |  |  |
| DNAP00118 | TAXOL | 2000-11-02 | null | CA125 | 2000-10-26 | 53 | AGAC/ATGC | brown | brown1 |
|  |  |  |  |  | 2000-11-21 | 58 |  |  |  |
| DNAP00118 | TAXOL | 2000-10-03 | null | CA125 | 2000-10-03 | 44 | AGAC/ATGC | brown | brown1 |
|  |  |  |  |  | 2000-10-26 | 53 |  |  |  |
| DNAP00118 | TAXOL | 2000-08-03 | null | CA125 | 2000-08-01 | 62 | AGAC/ATGC | brown | brown1 |
|  |  |  |  |  | 2000-08-19 | 53 |  |  |  |

| | | | | | | |
|---|---|---|---|---|---|---|
| DNAP00118 | TAXOL | 2000-07-13 | null | CA125 | 2000-07-11 | 55 | AGAC/ATGC | brown | brown1 |
| | | | | | 2000-08-01 | 62 | | | |
| DNAP00119 | TAXOL | 2000-10-20 | null | CA125 | 2000-10-19 | 1064.2 | ATGC/ATAC | black | black |
| | | | | | 2000-11-09 | 207.7 | | | |
| DNAP00119 | TAXOL | 2000-12-29 | null | CA125 | 2000-12-27 | 20 | ATGC/ATAC | black | black |
| | | | | | 2001-01-17 | 14.3 | | | |
| DNAP00119 | TAXOL | 2000-12-04 | null | CA125 | 2000-12-01 | 93.9 | ATGC/ATAC | black | black |
| | | | | | 2000-12-27 | 20 | | | |
| DNAP00119 | TAXOL | 2000-10-23 | null | CA125 | 2000-10-19 | 1064.2 | ATGC/ATAC | black | black |
| | | | | | 2000-11-09 | 207.7 | | | |
| DNAP00119 | TAXOL | 2000-11-13 | null | CA125 | 2000-11-09 | 207.7 | ATGC/ATAC | black | black |
| | | | | | 2000-12-01 | 93.9 | | | |
| DNAP00120 | TAXOL | 2000-10-16 | null | CA125 | 2000-10-04 | 74 | ATGC/ATAC | black | brown2 |
| | | | | | 2000-11-17 | 6 | | | |

FIG. 10B

| GENE | HAP SYSTEM | % | LEVEL | FST P value | Exact P value |
|---|---|---|---|---|---|
| CYP3A4 | TX3A41119 | 20 | individual | 0.00901+-0.0091 | 0.08572+-0.00395 |
| | | 20 | test pair | 0.00901+-0.0091 | 0.00000+-0.00000 |
| | | 50 | individual | 0.03604+-0.0148 | 0.23224+-0.00285 |
| | | 50 | test pair | 0.00000+-0.0000 | 0.00363+-0.00056 |
| CYP3A4 | TX3A41120 | 20 | individual | 0.32432+-0.0411 | 0.55956+-0.00676 |
| | | 20 | test pair | 0.55856+-0.0504 | 0.67434+-0.00771 |
| | | 50 | individual | 0.60360+-0.0490 | 0.92720+-0.00206 |
| | | 50 | test pair | 0.70270+-0.0425 | 0.81895+-0.00469 |

| SNPNAME | MARKER | LOCATION | GENBANK | INTEGRITY | TYPE |
|---|---|---|---|---|---|
| CYP3A4E7_117 | 664802 | 15746 | AF209389 | POLY | SILENT |

FIVEPRIME
CTGGGACTAGAGTCTGCACATTTAACTATGGGTGGTGTTGTTTTGTGCTTAGATGGTCCCTATCATTG
CCCAGTATGGAGAGATGTGTTGGTGAGAAATCTGAGGCGGGAAGCAGAGACAGGCAAGCCTGTCACCTTGAA
AGAGTAAGTAGAAGCTCAGCACCATGGGTTCTGAGCTGTCATGAACCCCTCCAGCTGCCTGCCATGGAGCT
GATATTCCTGCTGTTGGGTTATTCCAGTGACCAGAGGAGGTGGGGCAGCTGTGGTAATGCAACTTCAATGGG
TCTCCCAAGATGGGGCAGCTCCGATGAGGAGGTGGGGCAGCTGGGAGGAAAAGGATCTTCTCCCCTGTGCA
CAGGGGCCAGGGTTTACATATCCATTAAATTGTCACCTTGGATATATTCTAGAAGACTAAATATATCCTTTA
GGGGGAAAAAGTGTGATTGTACCAAAGTTTAAGCATGGAGAGTTATAATGGAGAACTTAGAATAACTTTGATCAT
TGGTATCTGTTGGTGGTCAGTGAGTAGGTTGGGAGAATACTAAATATTAAAATTCCATTCTTTTTTCCTCCA
TTCATGTTTTTTCTGAGGATATCAGTAGAATACTAGTAGGGCAAGCTATTATTGCTATCTACACTTACG
GTCTCAAAGAGAGAGGGTGGTAAAAACACTAGTTTGTCCTGGGCAGACCAGGATAGGTGGTCACTCACTTAGAAAT
CAGTAAAACAGGTGTAATCTGAGTTTGTCCTGGGCAGACCAGGATAGGTGGTCACTCACTATAGAAAT
TCCAAATCAAATTTGAGAGATATTTCTAGGAGCTCAGGACAACAGGGTACTGTTGCTTTGTAAAGTGCTGAAGA
GTATAGAGAATAAGGATGATATTTCTAGGAGCTCAGGACAACAGGGTACTGTTGCTTTGTAAAGTGCTGAAGA
GGAATCGGCTCTGGGCATAGAGTCTGCAGTCAGGCAATATCCACCATCTGTCTTGAGCCCTTAGGAAGAGTTA
ATTATTCTACTCTTGTTCTGCTGAAGCACAGTGGGTCTCTGTCTTCCTATGATGGGCTCCTTGATCTCAGAGGTAGGTCTAAT
ACTGTAGTTGTCTGATAGTGGGCTCTCTGTCTTCCTATGATGGGCTCCTTGATCTCAGAGGTAGGTCTAAT
TCAGTTCAGTGTCTCCATCACACCCAGCGTAGGGCCAGCTGCATCACTGGCACCTGATAACACCTTCTGA
TGGAGTGTAATAGAAGGTGATCATAGAGGAAGGATCTGAAAGTCTGTGGCTGTGTTGTCTTGACTGGACATG
TGGGTTTCCTGTTGCATGCATGGGCTAAAAAGGTAAAAAGGTGCTGATTTAATTTTCCACATCTTTCT
CCACTCAGCGTCTTTGGGGCCTACAGCATGTGATCACTAGCACACATCATTGGAGTGAACAT

FIG. 13A

VARIANT
Y

THREEPRIME
CTCTCAACAATCCACAAGACCCCTTTGTGGAAAACACCAAGAAGCTTTTAAGATTTGATTTTTTGGATCC
ATTCTTTTCTCTCAATAAGTATGTGGACTACTATTCCTTTAATTTATCTTKCTCTCTTAAAAATAACTGC
TTTATTGAGATATAAATCACCATGTAATTCAKCCACTTWAAATATACAGTTCAGTGATTTGTAGTACATT
TGAAGATATGTGTGACCATCATCATTTAAACTTTAAAACTTTTTGTCAATCTAGAGACCTCATACAT
TTTAGCTATCAGCCCCTGTCACAAACCCTGTCATCATATGCAACCACTAATCAACTTTCTGCTCTAT
GGATTTGCCTATTCTGGACACTTCGTATCATTCTTCTGCTCATCAGGGTTTTTATTCTCTAGTTCAT
GAATTTGTACTTAGTCTGGCATGAACATAGATTACTGATTTGTGATTTTTTGTTCCTCTAAATTTAGACATTACA
TACTATGTTGTGGCCATGAGCATAGATTACTGATTTGTGATTTTTTGTTCCTCTAAATTTAGACATTACA
GCTGTAACTTCCCTCTGAGCACTTCTATTGTGAGATTGTGTGGCCTATCACATCTTAGTTT
TGTTCACCTCAAAACTTCCACATATGTGAGTTTCTCAATTTCTTCCCTTATGATTTCTTATCTTTATTCCAT
ATTAATTAACTTAACTTCCACATATGCTGTGTATTGTAGATTCCCTTACTATTTCTTGAACAGCAAGATTAA
GATAGGTGACAGAGATATGCTAGATTATTCTGAGTTCTATTCTAGGAGACTGTAGTAGTCCAATAGAT AAAGGCAAAGAGATT
TTTTGAGCTTCAGATTATGATTTGTTCCTTTTATCCTTCAAAAGATGCACAAGGGCTGCTGATCTCACTGCTGTAGC
AGGGCATTGAATTTGTTCCTTTTATCCTTCAAAAGATGCACAAGGGCTGCTGATCTCACTGCTGTAGC
GGTGCTCCTTATGCATAGACCTGCCCTTGATGTCTTTTACTCTCTGGTTGGTAGAGAAAAACTAGAAGG
AATGGCTTCCAGTTGCACATTCACAATGAATTTCTTTTCTGTTTTTTGTTTTCCTACAGCAGTCTTC
GGTAAATTTGCACATTCACAATGAATTTCTTTTCTGTTTTTTGTTTTCCTACAGCAGTCTTC
CATTCCTCATCCCAATTCTTGAAGTATTAAATATCTGTGTGTTTCCAAGAGAAGTTACAAATTTTTTAAG

FIG. 13B

```
[Data]

[[Samples]]

SampleName="CYP3A4LOC3-1214-10_10"
        SampleSize= 19
        SampleData={
        H1      17      A T T
                        A T T
        H2      2       A G T
                        A T T
        }
        SampleName="CYP3A4LOC3-1214-10_10"
        SampleSize= 22
        SampleData={
        H1      1       A T g
                        A G t
        H2      19      A T T
                        A T T
        H3      2       A G T
                        A T T
        }
```

METHODS FOR THE IDENTIFICATION OF GENETIC FEATURES FOR COMPLEX GENETICS CLASSIFIERS

This application claims the benefit of U.S. Provisional Application Ser. No. 60/338,771 filed Dec. 3, 2001.

This patent hereby incorporates by reference a Sequence Listing on compact disc (CD) in accordance with 37 C.F.R. 1.821–1.825. More particularly, two CDs (one original and one duplicate copy) named DNAPRINT_SEQLIST have been submitted to the U.S.P.T.O., each of which includes the Sequence Listing in a file named "seq_listing" created on Jul. 10, 2002 and having a size of 4.27 KB.

BACKGROUND OF THE INVENTION

1. Field of the Invention

The present invention relates generally to methods for identifying genetic features of a particular complex genetic trait, and more particularly to software-based methods which utilize statistical analyses for identifying one or more haplotype systems, alleles of which are useful for predicting a particular complex genetic trait.

2. Description of the Related Art

Human beings differ only by up to 0.1% of the three billion letters of DNA present in the human genome. Though we are 99.9% identical in genetic sequence, it is the 0.1% that determines our uniqueness. Our individuality is apparent from visual inspection—almost anyone can recognize that people have different facial features, heights and colors, and that these features are, to some extent, heritable (e.g. sons and daughters tend to resemble their parents more than strangers do).

Few realize, however, that our individuality extends to our disease status, or an ability or inability to respond to and metabolize particular drugs. Drug-reaction traits are only one example of a complex genetic trait Drugs are referred to as "xenobiotics" because they are chemical compounds that are not naturally found in the human body. Xenobiotic metabolism genes make proteins whose sole purpose is to detoxify foreign compounds present in the human body, and they evolved to allow humans to degrade and excrete harmful chemicals present in many foods (such as tannins and alkaloids from which many drugs are derived).

Because variability in drug metabolism enzyme sequences is known to explain most of the variability in drug response, it can be tested whether single nucleotide polymorphisms (SNPs) within the common xenobiotic metabolism genes are linked to variable drug response. To do this, thousands of SNP markers in hundreds of xenobiotic metabolism genes can be surveyed. From learning why some people respond well to a drug (i.e. they have certain SNPs) while others do not (i.e. they do not have the certain SNPs), classifier tests can be developed. Classifier tests include chemicals called "probes" that help determine the sequence of a person at the SNP locus. The classifier test can determine the suitability of the patient for a drug before it is ever prescribed. This is commonly referred to as a "personalized drug prescription".

Detailed analysis of SNPs and haplotype systems are required prior to developing these tests. A "haplotype system" is a coined term in the present application which describes the set of diploid (2 per person) phase-known haplotype combinations of alleles for a given set of SNP loci in the world population. A haplotype may be viewed as a particular gene flavor. Just as there are many flavors of candy in a candy store, there are many gene flavors in the human population. "Phase" refers to a linear string of sequence along a chromosome. Humans have two copies of each chromosome, one derived from the mother and one derived from the father.

Assume that a person has, in their genome, the diploid sequences shown below in Text Illustation 1.

```
Position    1 2 3 4 5 6 7 8 9 10 11 12 13 14
Person 1:   A G T C T G C C C A  T  G  C
            A C T C T G C C C A  A  T  G  G
```

Text Illustration 1. A Hypothetical String of DNA Sequence in a Hypothetical Person.

The "sense strand" is shown for both the paternal and maternal chromosome. This pair of sequences is called a diploid pair which represents a small segment of the three billion nucleotide letters that make up the individual's genome. Positions 2 and 10 indicate positions where people (and in fact this person) exhibit variability. Each position of variability is known as a SNP (single nucleotide polymorphism), and there are two of them shown in Text Illustration 1. Assume that positions 2 and 10 are the only SNPs in this region of the human genome. In this case, people are identical in genetic sequence at all other letters in the string. Thus, in the entire human race, only an A is observed at position 1, either a G or a C at position 2, only a T at position 3, and so on. By convention, person 1 is called a G/C heterozygote at SNP1 and a C/A heterozygote at SNP2.

Text Illustration 1 can be re-written as shown below in Text Illustration 2.

Person 1: GC
    CA

Text Illustration 2. A more convenient way to represent Person 1 than Text Illustration 1, where only the variable nucleotides are shown. The GC refers to the sequence of Person 1's maternal chromosome (reading the sense strand only) and the CA refers to the sequence of Person 1's paternal chromosome (reading the sense strand only).

In Text Illustration 2, the non-SNP nucleotide positions are omitted for convenience. Text Illustration 2 conveys every bit as much information about the sequence of Person 1 as does Text Illustration 1, because it is assumed in genetics that unwritten nucleotides are not variable. Although there are seven nucleotide letters in between SNP 1 (at position 2) and SNP 2 (at position 10), they are the same in everybody and are therefore already known by de facto.

The genotype in Text Illustration 2 can be represented in even another way shown below in Text Illustration 3.

Person 1: GC/CA

Text Illustration 3. Haplotype pair as written by convention for Person 1.

The sequences GC and CA are called haplotypes. Person 1, as does everyone, has two haplotypes=1 GC haplotype and 1 CA haplotype. Thus, this individual can be referred to as a GC/CA individual One haplotype is derived from the mother (maternal) and the other is derived from their father (paternal). It is not known from this representation whether the paternal haplotype is the GC or the CA haplotype.

When a scientist reads genetic data from people, they generally only read the positions that are different from person to person. This process is called "genotyping".

Although it would be very convenient to read that person 1 has a GC sequence in this region of their maternal chromosome and a CA sequence at their paternal chromosome, it is most practical technically to read the diploid pair of nucleotide letters at SNP 1 and the diploid pair of letters at SNP2 independently.

What a scientist reads, therefore, is shown below in Text Illustration 4

Person 1: SNP1: (G/C) SNP2: (C/A)

Text Illustration 4. Genotype Reading from person 1. The Person has a G and a C at SNP1, and a C and an A at SNP2.

From Text Illustrations 1, 2, and 3 it can be seen that the person is a GC/CA individual, as written by genetic convention. From the representation shown in Text Illustration 4, however, this is more difficult to identify since the SNP genotypes can be combined in several different ways. For example, it is not known whether the individual has the GC/CA haplotype pair or the GA/CC haplotype pair; all that is known is that the individual has a G and C at SNP1 and a C and A at SNP2. It is possible, however, to use well-known statistical methods to infer that the person indeed harbors the GC/CA haplotype pair rather than the GA/CC pair. So inferring, Text Illustration 4 contains every bit of information as do Text Illustrations 1 through 3. The genotypes shown in Text Illustration 4 are called "phase-unknown" genotypes because it is not clear (before inference) whether the SNP genotypes are components of GC/CA or GA/CC haplotype pairs. After the phase has been determined as GC and CA, each haplotype is referred to as a "phase-known" genotype pair.

By definition, haplotypes are comprised of phase-known genotype combinations. Haplotype pairs are comprised of pairs of phase-known genotype combinations. In the example given (Text Illustrations 1–4), there are 2 SNPs within a stretch of 14 nucleotide letters of DNA from a particular segment of the genome. In actual practice, however, genes are much longer than 14 nucleotide letters long and a SNP is generally found once every few hundred nucleotide letters.

Regardless of its length in nucleotide letters, a gene containing 4 SNPs has a large number of 2-locus haplotype systems, a smaller number of 3-locus haplotype systems, and one 4 locus haplotype system. In FIG. 1, a gene 100 with a plurality of SNPs 102 is illustrated in a second example to help describe the concepts regarding a haplotype system. In this second example, gene 100 is one thousand nucleotides long and shown as a horizontal block. Arrows which extend from SNPs 102 to gene 100 identify four nucleotide positions within the gene sequence that may be different in different individuals. On the other hand, the remaining 996 nucleotides are identical in different individuals of the world population. Virtually all known SNP loci are bi-allelic, meaning that there are only two possible nucleotides found at that position in the population.

For the purposes of this example, the bi-allelic sites will be defined as SNP1=(A/T), SNP2=(G/A), SNP3=(C/T) and SNP4=(C/T). Given the laws of probability, this gene 100 has $$\sum_{j=2}^{n} {}^{n}C_j, \text{ where } {}^{n}C_j = \frac{n!}{j!(n-j)!}$$

possible n-locus haplotype systems, where n>1. One of these haplotype systems is:

SNP1: SNP2: SNP3: SNP4 which is a four-locus haplotype system. Given that SNP1= (A/T), SNP2=(G/A), SNP3=(C/T), and SNP4=(C/T), there are several constituent haplotypes that are part of this haplotype system. For example:

AGCC
AGTT
TGCC
etc.

Another haplotype system (a two-locus system) is:

SNP2:SNP4

Given that SNP1=(A/T), SNP2=(G/A), SNP3=(C/T) and SNP4=(C/T), there are several constituent haplotypes that are part of this particular haplotype system:

GC
GT
AC
AT

Each one of these haplotype systems has many different haplotype constituents that can be combined into an even larger number of haplotype pairs. For example, the SNP2: SNP4 haplotype system is represented within individuals (according to the laws of independent assortment) as the GC/GC pair, the GC/GT pair, the GC/AC pair, etc.

Ignoring dispersive genetic forces such as recombination and mutation which have shaped the genetic structure of the population, the sequence at one SNP is assumed to be independent of the sequence at other SNPs. This means that there are several possible haplotypes in the population of human beings for an N-locus haplotype system. In fact, from probability theory there are $2^N$ possibilities. For example, for a four-locus haplotype system where position 1 is A/T, position 2 is G/A, position 3 is C/T, and position 4 is C/T, there are $2^4=16$ possibilities:

```
AGGC, AGCT, AGTC, AGTT, AACC, AACT, AATC, AATT
TGCC, TGCT, TGTC, TGTT, TACC, TACT, TATC, TATT
```

In actual practice, however, there are usually fewer haplotypes in the population than one would expect because systematic genetic forces (such as population bottlenecks, random genetic drift and selection) have contributed to shape the structure of our population. This complication is important for the process of haplotype inference, but will be ignored as it does not significantly impact the present analysis.

As described earlier, a given individual has both a maternal and paternal copy of each chromosome to form a diploid pair. The genotype of any human being, with respect to the haplotype system, is written as a pair. A person written as AGCC/TATT, for example, contains one haplotype derived from the father and one from the mother. Since there are 16 possible haplotypes, there are $$n+[n!/(r! \times (n-r)!)]$$

(where n=the number of haplotypes, and r=2 for pairs) possible diploid haplotype combinations in the human population. Thus, from 4 SNPs, we see how there can be 124 types of people in the population; some are AGCC/AGCC, others are AGCC/AGCT, others AGCC/AGTT, and so on. When the number of SNPs is larger than 4, the numbers quickly become unmanageable. For example, if there are 8 SNPs in a gene, there are 256 possible haplotypes and several thousands of possible pairs of haplotypes in the population.

Using conventional analysis, scientists can sometimes determine whether a given haplotype system is useful for predicting disease status by determining whether trait-affected and non-affected individuals have different haplotypes for a given haplotype system. For example, consider a haplotype system with the possible values GC, GA, CA, CC. If a scientist notes that people who respond well to an anti-cancer drug always have the GC/GC haplotype pair, this scientist has identified the GA, CA and CC haplotypes as risk markers for non-response to the drug. However, this is a relatively simple haplotype system having only four constituents.

Now consider a ten SNP haplotype system where one SNP is the cause of a non-response trait. Referring to FIG. 2, haplotype pair data 200 from four people for a ten-locus haplotype system in a region of the genome relevant to an anti-cancer drug response are shown. Each of these positions illustrates a bi-allelic variant within a larger block of DNA sequence. The nucleotide letters that are the same from person to person are omitted by convention. The letters in column 2 for persons 2 and 4 denote sequence variants 202 that causes a non-response to the anti-cancer drug. Response status is shown in the last column.

The four person group of data shown in FIG. 2 may be representative of a larger group of patients. Conventionally, a scientist would first obtain genotypes for each patient at these ten positions and infer haplotypes for these persons as shown in FIG. 2. The scientist would then segregate responders from non-responders and measure whether there were statistically significant differences in haplotype constitution between the two groups. In the example of FIG. 2, persons 2 and 4 would be in the responder group and persons 1 and 3 would be in the non-responder group. Visually comparing the two groups, it is apparent that only position 2 sequences are distinctive between them: responders have 2 G's at position 2 and non-responders have 2 C's, while the sequence for the other positions is not different between the groups.

Under conventional analysis, however, most genetics researchers do not work at the level of the gene haplotype. About three quarters of researchers who study genetic variation focus on individual SNPs and attempt to draw associations between SNP genotypes and traits. This is called a simple genetics approach, with which there are two problems. First, these studies generally suffer from lack of statistical power to detect associations, a power that is imparted to haplotype studies by systematic genetic forces that have shaped the genetic structure of our modern day population. Second, they are inappropriate for solving complex genetic issues. Because most human traits are complex functions of intergenic (sets of SNPs and ploidy issues) and intragenic (i.e. multiple gene-gene interactions) factors, this is a serious limitation.

On the other hand, about one quarter of geneticists perform their work at higher levels of complexity. These geneticists consider genetic determinants at the level of the haplotype, rather than the SNP, and infer phase using computational methods or directly through biochemical means. Regardless of how phase is determined, haplotype systems are usually defined based on convenience. If a gene has 30 SNPs distributed throughout its sequence, for example, a researcher would likely select a small number of these SNPs as components of a haplotype system for study. This selection process is sometimes based on whether the SNP causes a coding (amino acid) change in the expressed protein, or rather based on the fact that the chosen SNPs cover the gene sequence well from 5' to 3' end. The problem with this approach is that it is somewhat arbitrary and leaves most of the SNPs in the gene untested even though they may be linked, within the context of a specific combination, to the trait under study.

Most human genes have about 30–50 SNPs. Thus, if variants for such a gene were the cause of the non-response trait, and this variability could be ascribed to one or two SNPs, most of the haplotype systems chosen for study would be worthless for predicting the trait (given the laws of probability). In other words, the alleles from haplotypes, comprised of those SNPs, would not be statistically associated with the trait. (The latter point is slightly complicated by a concept called linkage disequilibrium, but it does not significantly impact the argument presented.) This follows from the observation that there are a large number of possible haplotypes incorporating these SNPs (i.e. $2^{30}$–$2^{50}$, 30 and 50 SNP haplotype systems, respectively) and an even larger number of haplotype pairs in the human population for each gene. The reason why single-SNP analysis should not be relied upon is that SNP alleles may be more rigorously associated with a trait within the context of a combination of other SNPs rather than on its own (which is frequently found to be the case), due to the genetic structure of the population.

What this means for scientists trying to solve vexing disease and drug-response traits is there is a large amount of data to sift through in drawing statistical associations between haplotypes, or haplotype pairs, and commercially relevant human traits. For most human genes, the number of haplotype systems that could possibly be invoked to explain variable traits in the human population is far larger than the number that actually explain them. This poses a tremendous statistical barrier for current day genetic research.

As apparent, a significant problem with conventional methods is that there is no logic or computer software that exists to predict which sets of SNPs define the optimal haplotype system for understanding the trait. In some cases, a short haplotype system may prove optimal. In other cases, a long haplotype system may prove optimal. In either case, there is no way to predict which will be the case.

A long haplotype system may best explain the variability in a certain trait due to the complexity of the trait. For example, assume a trait is associated with and caused by the coincidence of 4 minor SNP variants such that a haplotype with minor alleles at (at least) any two of these four SNP positions is required in order for the trait to be expressed, and only people with the haplotype comprised of at least 2 minor alleles at these SNP locations reveal the trait. Also assume that research scientists are trying to understand the genetics of this trait. The scientists know there are 15 SNPs in this gene, but due to the large number of possible haplotype systems they have randomly chosen only a few for analysis.

Further assume that one of these chosen haplotype systems has only 2 of the 4 SNPs. When the trait-affected and non-affected groups are partitioned, and the haplotype constitution of each group is visually inspected, they would indeed notice that minor alleles for these 2 SNPs were found only in the affected group. Also, there would be many affected that did not have minor alleles at these 2 SNP locations, or had minor alleles at only one of the 2 SNP locations. In fact, because it is known that at least 2 minor alleles at the 4 SNP locations are required for the affected status, these individuals must have minor alleles at one or both of the other 2 SNPs that were not part of the haplotype system. In this case, a longer more complicated haplotype system would be optimal for describing the relationship between the gene and the trait.

On the other hand, a short haplotype system may best explain the variability of certain traits for two main reasons. First, short haplotype systems have fewer possible haplotypes and fewer diploid haplotype combinations than do long haplotype systems. Geneticists do not have the luxury of genotyping whole populations and usually rely on cohorts that are representative of the population. For certain traits, these cohorts may be limited in size for several reasons. When studied with long complicated haplotype systems, these cohorts produce numerous genetic classes of sample sizes that are too small to prove that they are related to the trait. It is well known to those skilled in the art of statistical genetic analysis that, given a constant study sample size, the larger the number of possible classes, the lower the sample size within each class. Small sample sizes in haplotype classes of complicated haplotype systems could conceal a statistical relationship even if the haplotype system is the optimal system for describing the relationship of the gene with the trait. Thus, in genetics, the "statistical power" of long, complicated haplotype systems can be lower than that of smaller ones.

Secondly, short haplotype systems can more concisely explain trait variance when a specific sub-region of a gene is relevant for the trait. In this case, if a small domain of a gene causes a particular trait, a small haplotype system comprised of SNPs found within this domain would be expected to genetically define the trait better than a larger, more complicated system incorporating these same SNPs. This is because SNPs found in other regions are not relevant for the trait, and serve to only complicate the analysis. In many cases, variance among these irrelevant SNPs can statistically conceal the associations of the relevant ones.

Some geneticists work strictly within the context of "whole gene" haplotypes. A common argument for this approach is that no functionally relevant SNPs can be missed. Since both the low statistical sample size within each genotype class and the fact that irrelevant SNPs can conceal the statistical significance of relevant SNPs, this method is far from optimal. Others geneticists select SNPs that span a gene from end to end and attempt to identify functionally relevant haplotypes using an approach that tracks unseen variants embedded in the structure of a haplotype cladogram. A haplotype cladogram is an evolutionary tree describing how the haplotypes relate to one another in sequence, and over evolutionary time. Although this approach sometimes provides good results, it performs relatively sub-optimally in cases where statistical sample size is a consideration as well as in cases where the biology of the trait is a function of a small domain within the gene. It is also subject to statistical limitations imposed by the specific SNP loci selected for analysis.

Thus, identifying the set of SNPs that most efficiently explain the variance of a trait is a crucial, but non-trivial task for developing complex genetics classifiers. Haplotype systems are "genetic features" in that they can be used, to an extent, to distinguish among individuals and groups of individuals. The present application coins this term to represent haplotype systems as component pieces of a given complex genetics puzzle (i.e., a typical human trait). The best, most informative haplotype systems are crucial for any effort to identify genetic features of adequate predictive value for use in a clinically useful classifier test. Complex genetic solutions developed from sub-optimal haplotype systems (i.e. SNP combinations that explain less of the trait variance than contributed by the gene within which they are found) are restricted in utility and accuracy by the limitations of the constituent haplotype systems.

Thus, there are important reasons to find the optimal haplotype system that explains a trait for developing a classifier test. This optimal haplotype system may be a short one for certain traits and genes, but a long one for others. A haplotype system with 16 SNPs covering an entire gene may be the optimal system for a given trait and a given gene, for example, but a short 2 SNP haplotype system may be the optimal system for describing the relationship between this same gene and a different trait. In fact, there are no consistent rules a scientist can use to predict what sort of haplotype system should be selected in any given situation. The identification of the optimal haplotype system is in some ways a matter of trial and error, but given the large number of possible haplotypes for even short haplotype systems, it is not a task which should solely involve human analysis and inspection.

The difficulty is that computational tools for this process do not currently exist, and it is this need that is addressed by the inventive methods and apparatus described in the present application. On the other hand, there are various existing software applications that could serve as individual components of such a pipeline system. For example, consider the inventive "feature extraction" method. Some existing programs are designed for calculating whether alleles of a given haplotype system are useful for resolving between trait classes. For example, see Raymond, M. and F. Rousset, "An exact test for population differentiation," 1995, Evolution 49(6), 1280–1283. However, there are no software applications which incorporate such a method into a systematic feature extraction process.

Other conventional software applications make the above-described test somewhat more convenient for the geneticist. For example, the Arlequin™ software program is one such program. These applications, however, require numerous manual manipulations. For example, the Arlequin™ program requires the user to retrieve SNP data for a given SNP combination for inspection and to create a text input file containing the genotype and phenotype data relevant for the inspection. It takes about thirty minutes, for example, for a scientist skilled in the art to retrieve this data and create the file. When the "Exact test" of the Arlequin™ program is completed, the user would have to create a second file for the next SNP combination, and so on.

Given that patients are genotyped at several tens of SNPs per gene, tens of thousands of possible SNP combinations need to be tested in order to assure that the optimal combination has been identified (assuming that a useful system for that gene does indeed exist). This would require many months of the scientist's time. Even still, this work would only address a single gene. When additional genes are added to the analysis, the process would take an average scientist years to perform using currently available software tools and algorithms. What is needed is a software pipeline system that takes care of each of these manipulations automatically. Rather than forcing a scientist to spend years creating text files and logging results, a software system is needed which performs such processing in minutes. This system should integrate a combination of statistical tests, algorithms, and software applications into an automated informatics platform.

Other components of the software system have ideological and practical counterparts in existing methodologies. One or more software-based statistical tests may be used to evaluate a haplotype system as a genetic feature. Ideas for one these tests were first propounded by Raymond and Rousset. See, e.g., Raymond, M. and F. Rousset, "An Exact Test For Population Differentiation", Evolution 49(6), 1280–1283, 1995. As we have described earlier, however, if a scientist desired to use Raymond and Roussets' algorithm to do the type of work we have described, it would take them years to do a job that the inventive platform system would take only days to do. Ideas for another test, the F-statistic test, were first propounded by Fisher. See Fisher, R. A., "The Logic of Inductive Inference," Journal of the Royal Statistical Society 98:39–54, 1935.

The modeling algorithms and software applications that function downstream of the haplotype feature extraction system are also novel applications of existing methods for genetic analysis. Correspondence analysis for complex genetic analysis is believed to be a novel and non-obvious methodology, although correspondence analysis has previously been used by sociologists to model sociological variables and by mechanical engineers to model physical variables. This is also true for the linear & quadratic as well as the classification tree techniques for complex genetics analysis. The process of drawing haplotype cladograms (part of a geometric modeling method) was introduced by Templeton et al., 1995. Although methods for drawing these haplotype cladograms have been previously described, it is believed that a method for encoding and plotting haplotypes in geometrical space, based on their position within a haplotype cladogram, for the extraction of complex genetics information, is also novel and non-obvious.

Other relevant publications include Shou M, Lu, T, Drausz, K., Sai, Y., Yang, T., Korzekwa, K R., Gonzalez, F., Gelboin, H., 2000, "Use of inhibitory monoclonal antibodies to assess the contribution of cytochromes P450 to human drug metabolism," Eur J Pharmacol 394(2–3):199–209; and Dai, D., Zeldin, D C, Blaisdell, J., Chanas, B., Coulter, S., Ghanayem, B., Goldstein, J., 2001, "Polymorphisms in human CYP2C8 decrease metabolism of the anticancer drug paclitaxel and arachidonic acid," Pharmacogenetics 11(7): 597–607.

Accordingly, what are needed are methods and apparatus for quickly, efficiently, and accurately identifying associations between genetic features (e.g. haplotype systems) and genetic traits of individuals.

SUMMARY OF THE INVENTION

Methods and apparatus for identifying associations between genetic information and particular genetic traits are described. A candidate single nucleotide polymorphism (SNP) combination is selected from a plurality of candidate SNP combinations for a gene associated with a genetic trait. Haplotype data associated with this candidate SNP combination are read for a plurality of individuals and grouped into a positive-responding group and a negative-responding group based on whether predetermined trait criteria for an individual are met. A statistical analysis on the grouped haplotype data is performed to obtain a statistical measurement associated with the candidate SNP combination. The acts of selecting, reading, grouping, and performing are repeated as necessary to identify the candidate SNP combination having the optimal statistical measurement. In one approach, all possible SNP combinations are selected and statistically analyzed. In another approach, a directed search based on results of previous statistical analysis of SNP combinations is performed until the optimal statistical measurement is obtained. In addition, the number of SNP combinations selected and analyzed may be reduced based on a simultaneous testing procedure.

BRIEF DESCRIPTION OF THE DRAWINGS

FIG. 1 is an illustration of a gene having a plurality of single nucleotide polymorphisms (SNPs);

FIG. 2 is data which show different haplotype pairs of four different individuals, showing nucleotide sequences illustrated in consecutive order which are numbered as follows:
SEQ ID NO: 3;
SEQ ID NO: 4;
SEQ ID NO: 5;
SEQ ID NO: 6;
SEQ ID NO: 7;
SEQ ID NO: 8;
SEQ ID NO: 9;
SEQ ID NO: 10;

FIG. 3 is an illustration of computer devices of a computer network;

FIG. 4 is an illustration of various computer components which may embody or operate to perform the methods of the present invention;

FIG. 8 is an example of data which show all known SNPs of a particular gene;

FIGS. 9A–9B is an illustration of a portion of a first HTML file that is created by the methods;

FIG. 10 is an illustration of a second HTML file that is generated by the methods;

FIG. 11 is haplotype data of the present example which is grouped into a responding group and a non-responding group;

FIG. 12 shows data which reveal the statistical measurements of two haplotype systems;

FIG. 13 is display data which identifies the optimal haplotype system of the present example, showing nucleotide sequences which are numbered as follows:
SEQ ID NO: 11;
SEQ ID NO: 12; and FIGS. 14–18 are illustrations of displayed output.

DETAILED DESCRIPTION OF THE PREFERRED EMBODIMENTS

Figure 5:
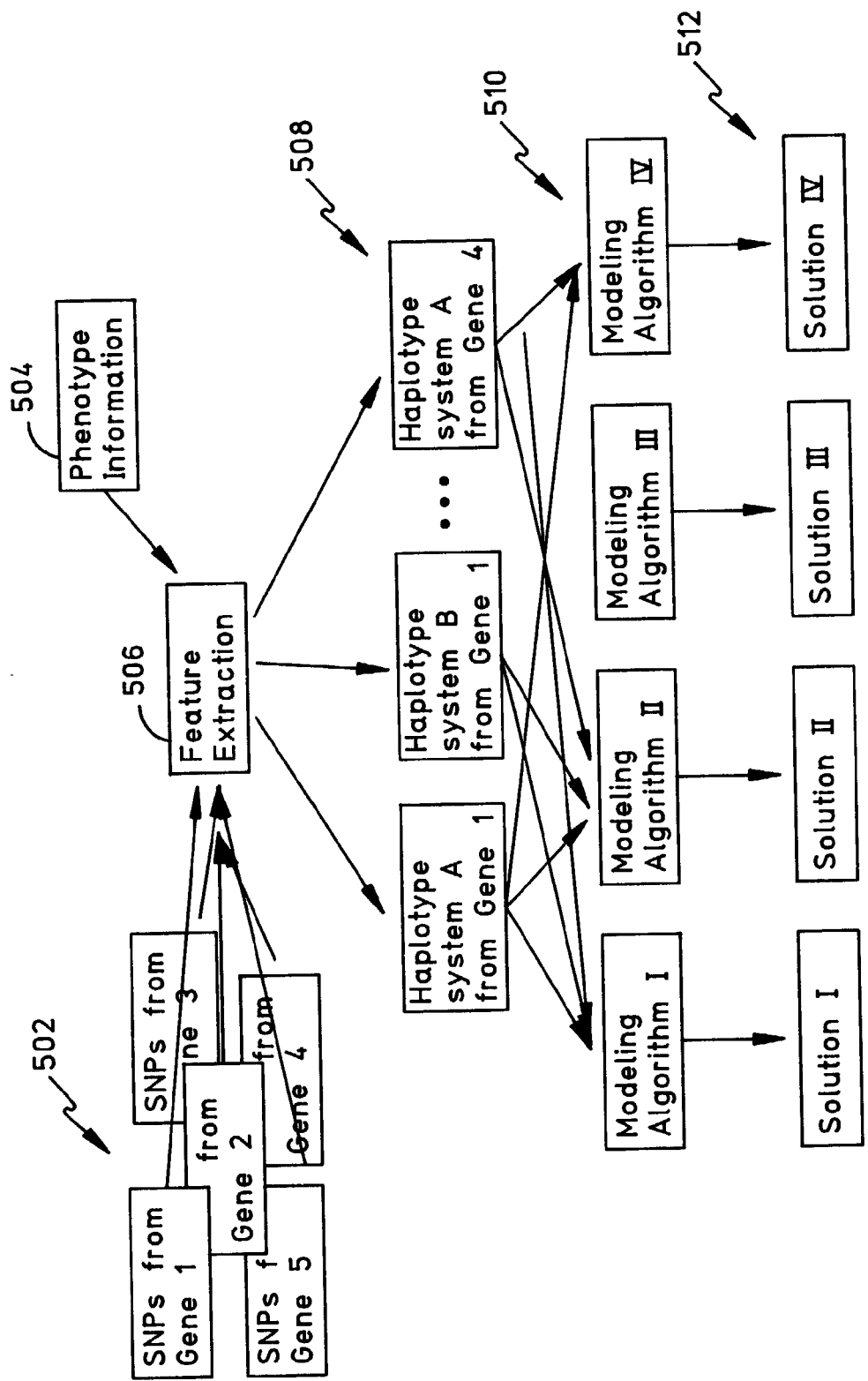
FIG. 5 is a flow diagram for a general overview for the methods of the present invention.

How a patient responds to a drug, and whether they acquire a disease, is a function largely of their genetic background. There is considerable interest in developing genetic solutions for a number of clinically relevant human traits. However, the problem in the field is that most genetics research is conducted on simple genetics terms, and most of the tools available to researchers are simple genetics tools. Most human traits are complex (involving multiple gene sequences) and the simple genetics analysis of complex genomics data rarely yield classifiers that are sensitive or accurate enough to be used for patient classification. The availability of the human genome map allows complex genetic analysis on a scale never before possible, but in order to realize its potential researchers must learn how to study genomics data in complex genetics terms. In the near future, physicians may use patient classifiers to determine whether a patient will respond to one type of medication or another, or whether a certain medication will cause sideeffects in a patient Physicians may also be able to predict disease in a patient based solely on their genetic background.

Advantageously, what has been developed is a novel and superior software-based method for identifying, from high-density SNP arrays, the most informative haplotype systems (or "genetic features") for solving complex genetic traits. Having identified the optimal haplotype features, additional analytical methods can be utilized for the development of patient classifier tests. The methods described herein are among the very first complex genetics analytical tools. As such, they enable the production of classifier tests of unprecedented sensitivity, specificity and accuracy. Because only the most sensitive, specific, and accurate testing products will pass Federal Drug Administration (FDA) scrutiny and find a commercial market in the clinic of the future, the tools described herein impart a tremendous commercial advantage.

The methods and apparatus described involve a more systematic approach for haplotype screening. Broadly, the method is to (1) genotype patients at all the known SNPs for a gene; and (2) use a computational method for identifying which combination of SNPs best explain the trait (if any). The detailed method of haplotype screening is superior to the method employed by others in the field because it allows an unbiased, assumption-free, and comprehensive identification of genetic markers and sets of markers that most efficiently explain the trait. The computational methods for accomplishing this are the subject of this patent application. More particularly, the invention pertains to a software system which tests a plurality of haplotype systems within a gene for those with alleles that have an ability to explain the variance of a trait.

In one embodiment of the present invention, all possible haplotype systems are defined and tested for statistical association with the trait so that the haplotype system having the optimal statistical measurement is identified. However, since the number of haplotype systems can be large, and since the analysis of each haplotype system involves multiple steps, systematically testing all possible haplotype systems could take weeks even with use of expensive computer hardware. Thus, a second embodiment of the invention makes use of artificial intelligence and other techniques in order to more quickly cull out the best haplotype systems from the rest. In this embodiment, some number of haplotype systems, but not all, are tested. As the algorithm tests selected haplotype systems, it learns which SNPs are important and biases its haplotype selection process to include those SNPs. As the method proceeds, it hones in on the optimal haplotype system until it is identified.

The general components of the invention include: (1) a database management system that retrieves relevant genetic and phenotype (trait) data for a given problem. The user defines markers to consider (i.e. those within a certain gene) and the trait through a graphical user interface; (2) a process for generating a text file report for visual inspection of each step along the path of problem definition, data collection, and data analysis; (3) a process for selecting a haplotype system for analysis, organizing the data relevant for testing the haplotype system, statistically calculating the haplotype system for analysis, and generating a dynamically updated results file that stores the haplotype system identifier and associated statistical measurements.

FIG. 3 is a block diagram of a computer system 101 which may embody the present invention. Computer system 101 includes a network 103 as well as networks 104 and 106. Network 103 is publicly accessible, and a server 108 and a database 110 which are coupled to network 103 are also publicly accessible. On the other hand, computer networks 104 and 106 are private. Each one of computer networks 104 and 106 include one or more computing devices and databases. For example, computer network 104 includes a computing device 112 and a database 114, and computer network 106 includes a computing device 116 and a database 118. The computing devices may include any suitable computing device, such as a personal computer (PC), a laptop computer, or a hand-held wireless device.

Network 103 may be the Internet, where an Internet Service Provider (ISP) is utilized for access to server 108 and database 110. Database 110 stores public domain gene data. Also, the inventive software is preferably used in connection with and executed on computing device 112 of private network 104. Although a preferred computer system is shown and described in relation to FIG. 3, variations are not only possible, but numerous as one skilled in the art would readily understand. For example, in an alternative embodiment, network 103 may be an Intranet and database 110 a proprietary, private DNA sequence database.

The methods described herein may be embodied and implemented in connection with FIG. 3 using software components 201 shown in FIG. 4. The software may be embedded in or stored on a disk 203 or memory 204, and executable within a computer 206 or a processor 208. Thus, the inventive features may exist in a computer readable medium which embodies computer program instructions which are executable by a computer or computer processor for performing the methods.

Such software is preferably used in connection with and executed on computing device 112 of private network 104. Preferably, the system functions within the context of a PC network with a central Sun Enterprise server. The program can be loaded and run on any desktop PC that operates using the Linux or Unix operating system. Other versions could also function in a Windows environment. Alternatively, the software could operate on a publicly accessible server and available for use through a public network such as the Internet.

General reference to FIG. 5 will now be made. What has been invented is an informatics pipeline system for the efficient and accurate discovery and modeling of genetic features. More particularly, this is a computational pipeline whereby large amounts of value-poor data are input and smaller amounts of value-rich data are produced. More particularly, SNP genotypes and phenotype data are the input data and multivariate solutions relating the various haplotype systems to the trait are the output. The process can be thought of as a sieve or a funnel in that the most informative SNP combinations are culled from many possible combinations and then fit together in the best way possible. Combined with the information about how they fit together to explain the trait, the marker sets constitute a tool that can be used to predict trait values from genotypes.

There are two phases of the process. In the first phase, the pertinent genetic features are identified; in the second phase, the best model for using these genetic features to make genetic predictions is picked. In the first phase, many SNP combinations are tested for the ability of their alleles to resolve between trait classes. In the second phase, the features identified during the first phase are fit together using one or more different mathematical approaches. From an input that could include well over 1,000,000 data points and several hundred Megabytes of data (genotypes, clinical tests, etc.), the best possible "solution" present in the data is extracted. The solution could represent one Kilobyte of data or less, depending on the software application used for its presentation and use.

The block diagram in FIG. 5 is an overview of the process for extracting and modeling genetic features for the development of genomics patient classification tests. Genotype data 502 for a plurality of patients at numerous SNP positions are merged with the patient's phenotype data 504. Data 502 and 504 are input into a feature extraction process 506 to identify genetic features 508 (one or more SNP combinations or haplotype systems) that are useful for genetically distinguishing between trait classes. Feature extraction process 506 only identifies which genetic features are important; however how they fit together (if they fit together at all) is determined by one or more statistical modeling algorithms 510 to produce one or more solutions 512. That is, once the features have been identified, the modeling algorithms are executed to weave the features into a complex genetics tale. The present invention described herein relates more particularly to feature extraction process 506.

One software-based modeling algorithm is described herein (namely, the linear and quadratic analysis), although such algorithms are generally outside the scope of the present invention. Other software-based modeling algorithms may be utilized, alone or in combination, such as a classification tree analysis and a correspondence analysis, as described in U.S. Provisional Application Ser. No. 60/338,771 filed Dec. 3, 2001, which is hereby incorporated by reference herein.

Figure 6:
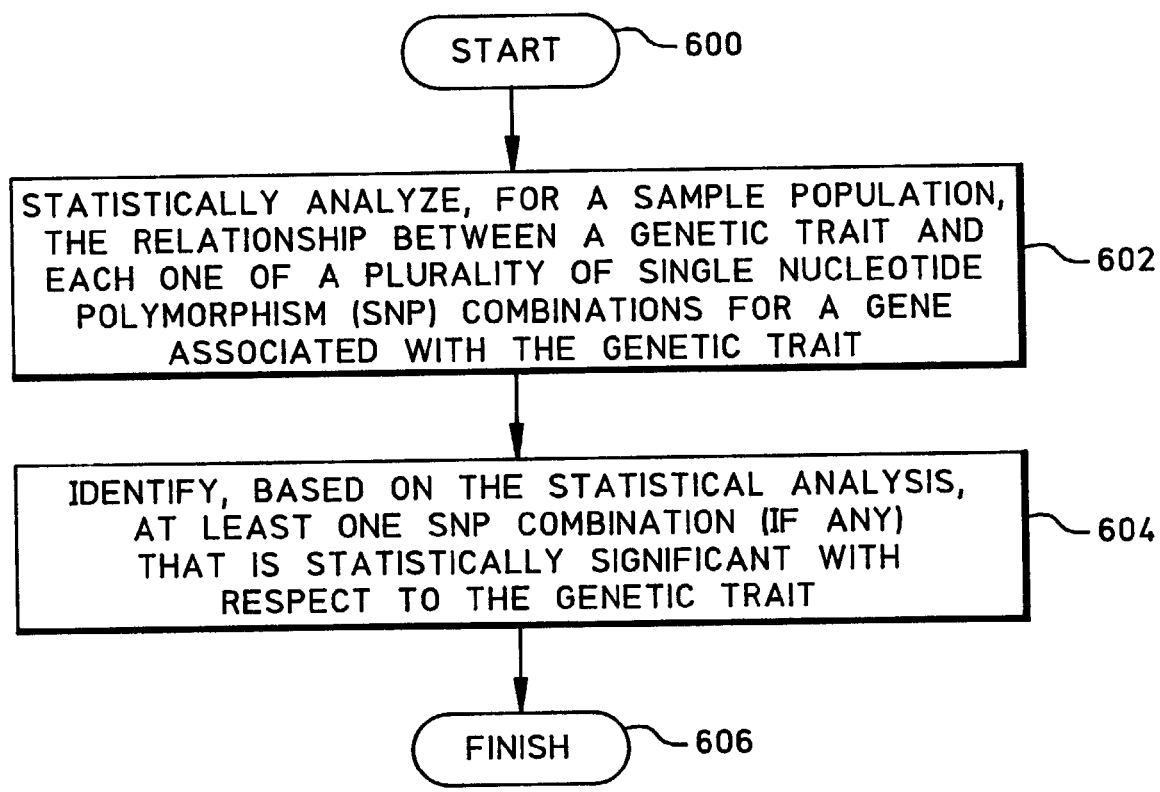
FIG. 6 is a general flowchart which describes a method of the present invention.
Figure 7:
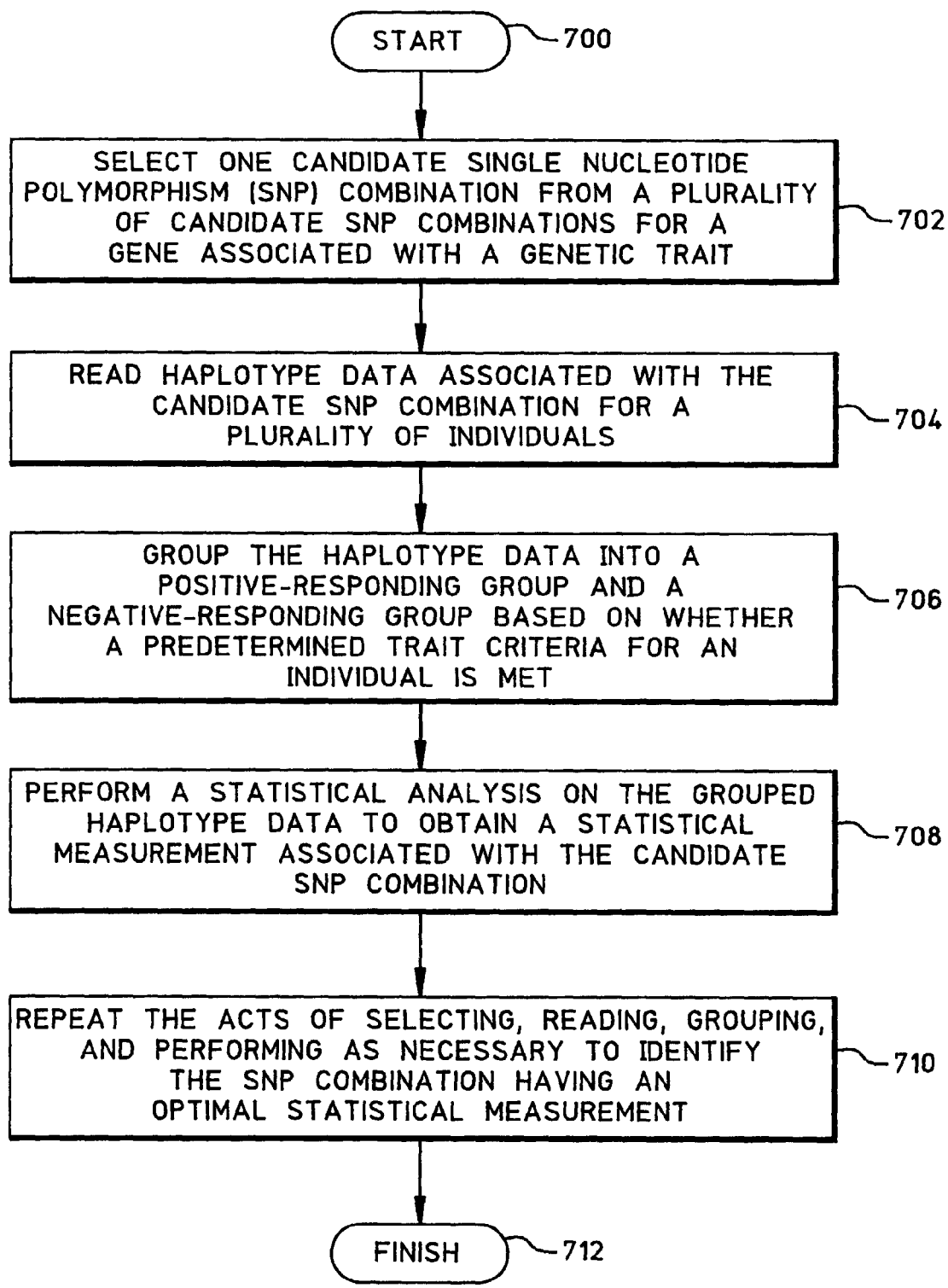
FIG. 7 is a flowchart which describes the method of the present invention in more detail.

FIGS. 6 and 7 are flowcharts which describe methods for identifying haplotype system features of genetic traits. FIG. 6 is a basic flowchart relating to the methods, whereas FIG. 7 is a more detailed description thereof. These methods are used in connection with software components 201 of FIG. 4 in the systems described in relation to FIG. 3. Beginning at a start block 600 of FIG. 6, a statistical analysis is performed on each one of a plurality of single nucleotide polymorphism (SNP) combinations for one or more genes associated with a particular genetic trait (step 602). This analysis is performed on data of a selected sample population. Next, at least one SNP combination that is statistically significant with respect to the genetic trait is identified based on the statistical analyses (step 604), if one exists at all. The flowchart ends at a finish block 606.

The more detailed method in the flowchart of FIG. 7 will now be described. Beginning at a start block 700, one candidate SNP combination from a plurality of SNP combinations for a gene associated with a particular genetic trait is selected (step 702). Step 702 of FIG. 7 may be performed in computer device 112 of FIG. 3 by what is referred to as a data selector, which is a data selecting process. Next, haplotype data associated with this candidate SNP combination for a plurality of individuals of a sample population are read (step 704). Step 704 of FIG. 7 may be performed in computer device 112 of FIG. 3 by what is referred to as a data reader, which is a data reading process. This haplotype data is grouped into a positive-responding group or a negative-responding group (or alternatively, trait-exhibiting or non-exhibiting groups) based on whether a predetermined trait criteria for an individual is met (step 706). Step 706 of FIG. 7 may be performed in computer device 112 of FIG. 3 by what is referred to as a data grouper, which is a data grouping process. Preferably, this step is performed by examining phenotype data of each individual.

Next, a statistical analysis is performed on the grouped haplotype data to obtain a statistical measurement for whether the allele sequence content differs between the groups (step 708). This is a measurement that is specifically associated with the candidate SNP combination. Step 708 of FIG. 7 may be performed in computer device 112 of FIG. 3 by a statistical analysis processor. The acts of selecting, reading, grouping, and performing are then repeated as necessary to identify one or more candidate SNP combinations with optimal statistical measurements (step 710). The repeating of steps may be decided by what is referred to as a decision component in computer device 112 of FIG. 3. When such SNP combinations (if any) are identified, the flowchart ends at a finish block 712.

In one embodiment, steps 702–708 are repeated such that each and every possible SNP combination from all possible SNP combinations is selected and statistically analyzed. Here, when the SNP combinations are selected, they are done so lexigraphically using random number generation. In an alternate embodiment, steps 702–708 are repeated such that the SNP combination selection is done in a "directed" fashion to find the optimal solution more quickly and efficiently, without having to test SNP combinations that are not likely to be optimal. In addition, the number of SNP combinations to statistically analyze are reduced based on a simultaneous testing procedure (STP). These embodiments will be described later in more detail.

Thus, the methods offer attractive and efficient ways to systematically "mine" available data for genetic features that help explain genetic traits. In particular, the inventive methods provide an invaluable tool to research teams for the development of genetic classifier tests for matching patients with drugs. If there is no value inherent in the available data, the system provides this information. Additional data is then tested from the patients at other SNPs in other genes. The results depend on not only the biology of the trait, but the character of the data available for the run. Some runs may take weeks, others hours. Some may produce models that explain almost all of the variation in the trait, whereas others may produce models that explain relatively little or even none of the variance.

The present methods will now be described in more detail. The performance of the informatics pipeline is a function of the data input. The data input is a function of the data that is available and the user's preferences. The database of genotypes and clinical information is the first restriction; a genetic relationship can only be searched for if the raw genetic and phenotype data relevant to the problem is available. The user selections form the second restriction; a scientist may wish to focus the informatics system on a subset of the available data for various reasons.

A user selects and enters the gene to be tested and the set of SNPs within the gene that the program should consider. The genetic trait to be analyzed is also selected. For drug reaction traits, for example, the user defines the drug(s) and the clinical test(s) relevant for measuring the patients drug response. The user also defines how the program should stratify the patients when performing statistical analysis. For example, the user may instruct the program to separate the patients into 20% responders versus non-responders, based on the test readings after the drug is taken (versus before). Combined, these user definitions make up the job which is to be processed.

The genetic features which will be identified will only be found in the selected set of genes for which genotypes and phenotypes are available in the database. For example, consider a variable response to a drug called LIPITOR™, which is a registered trademark of Pfizer Inc. Assume that LIPITOR™ patients have been genotyped at every known SNP within the following genes (and thus genetic data for each gene in each patient in the database are available):

TYR, CYP2D6, CYP3A4, CYP2C9, CYP7, CYP2E

These six genes form the first limitation to the process. The search for a genetic cause of variable LIPITOR™ response is only searched for within these six genes. If variable LIPITOR™ response is caused by variants of another gene that is not part of this list, the application of this informatics pipeline would be futile. The systematic character of the informatics platform ensures that if any of the six genes (or gene combination) causes or is linked to variable LIPITOR™ response, these genes will be identified. More importantly, the relevant SNP combinations expressing this linkage are found and assembled into an abstract model that can be used to classify patients based on their genetic values for these SNPs. Thus, the first constraint on the performance of the system is the input data and its relevance for the trait for which a solution is desired.

The second constraint is imposed by the user. Continue to assume that a classification solution for LIPITOR™ response is to be found. TYR is a pigmentation gene and has nothing to do with drug metabolism or drug disposition as far as medical science knows. The other five genes are known to be involved in drug metabolism (their names start with CYP indicating that they are cytochrome P450 genes=xenobiotic metabolizers). In fact, LIPITOR™ is known from the scientific literature to be metabolized by CYP3A4 (which is on the list) and therefore SNPs within this gene would certainly be included in a "run" of the system. See Casciano, W. et al., Hmb-CoA Reductase Inhibitors (Statins) Characterized As Direct inhibitors Of P-glycoprotein, Pharm Res, June 2001,; 1816: 800–6. CIn fact, it is shown below that this is the only gene identified to have associations using the system. This result confirms the sensitivity and specificity of the method.

When a job is submitted on the system, the SNPs or classes of SNPs corresponding to specific genes are selected for analysis. The job may query all of the SNPs within all of the genes, a subset of SNPs within all of the genes, or a subset of the SNPs within a subset of the genes. Usually, one selects the subset of genes from this list of genes with available SNP genotypes that are relevant for the trait to be found. The genes selected could, for example, be:

CYP2D6, CYP3A4, CYP2C9, CYP7, CYP2E

Alternatively, a quicker run can be performed by focusing on the following two genes:

CYP2D6, CYP3A4

To justify such a decision, it is up to the scientist to balance the comprehensiveness of a given screen with time and computational resource allotted for the run. A scientist with a large number of genetic problems to solve may want to focus the run on only two of five candidate genes because of hardware limitations.

For example, because CYP2D6 is known to be involved in the metabolism of 25% –60% of known drugs (depending on the cited reference), and CYP3A4 is known to metabolize LIPITOR™, these two could be selected. The run would be faster than the six gene run, and if LIPITOR™ disposition was a function of only these two genes, it would have been a wise choice. If it turns out that variations in CYP3A4 and CYP2E sequence explain 100% of the variance (say 60% and 40%, respectively), this would have been a poor choice and the best solution possible from the CYP2D6+CYP3A4 screen would have explained only 60% of the variance in LIPITOR™ response (that contributed by CYP2D6).

A long list of genes can be selected to cover all of the possibilities in order to make the run as comprehensive as data resources allow. However, this comprehensiveness is provided at the expense of resource devotion. Balancing the comprehensiveness of a run against available hardware resources and workload waiting list can be a difficult task to perform well. Preferably, the pace towards the final solution is continuously monitored by accumulating a running tabulation of percent variation explained. Thus, when a suitable amount of variation has been explained by discovered and modeled features, the run can be stopped. With this feature, the user does not need to extensively and blindly guess at which and how many genes and SNPs to consider. In effect, the optimal balance between computational effort and the quality of the output results can be found. This feature is important when one considers the time constraints imposed by the use of the system components.

The program then retrieves the relevant data for this job from the database (e.g., an Oracle database). Once retrieved, the program writes the results to a special file (e.g., an HTML file) for user inspection. This file allows the user to validate the job prior to execution of the haplotype selection and testing routine. This is important because the haplotype selection and testing routine could take several days to run until completion, depending on the complexity of the job. This file represents the first job report and is saved in a folder for later reference. All of the data which defines the job is part of this file: the genotypes for each SNP for each patient that qualified for (contained data for) the trait; the drug, test and/or trait for each of these patients; and any biographical data requested (e.g., race, sex, etc.).

Once approved by the user, the job is processed by the haplotype selection and testing routine. The program computes all possible haplotype systems (i.e. all possible SNP combinations) using the list of haplotypes defined in the job. More particularly, a haplotype system is selected and individual patient genotypes for this SNP combination are written to a text file. This text file serves as the input for another software component which is used to infer the phase corresponding to the haplotype system. This component may be a third party program, such as PHASE by Stephens and Donnelly, 2001, or Clark's algorithm. Once the phase has been determined for each patient, the results are written to another text file which contains the diploid pair of haplotype sequences for each person part of the job. This text file serves as input to another software component which replaces the phase-unknown genotypes of the HTML file with the diploid pair of phase-known haplotypes.

The program then stratifies or groups the patient data based on the previous user input regarding the genetic trait to be studied. This stratification produces (1) a list of haplotype pairs for a "responder" group and (2) a list of haplotype pairs for a "non-responder" group. Next, a statistical test (such as chi-square test, exact test, or a pair-wise F statistic test) is applied to the two groups of data in order to determine whether there is a statistically significant distinction between the haplotype constitution of the two groups. The statistical value for the test is written to a results file. The process is then repeated to select and test the next selected haplotype system.

In one embodiment, the process repeats until all possible combinations of SNPs have been selected and statistically analyzed. For a simple haplotype system, the program may take a couple of hours to run. For complex haplotype systems, it may take several days, depending on the length of the system. Another embodiment works generally in the same manner, except that it uses previous statistical results to guide the haplotype selection process. For example, if two particular haplotype systems have previously been determined to result in statistical values that meet a certain criteria (e.g., p-values that are below a certain threshold), and both systems contained a common SNP, the selection process is biased towards haplotype systems containing this common SNP. This eliminates consideration of SNPs that are unlikely to contribute meaningfully towards the optimal haplotype solution. Thus, the number of haplotype systems tested can be greatly reduced to result in a significant savings of time to identify the optimal one.

Time Constraints. The run time for the Haploscope program depends on the number of SNPs considered within the gene. If the number of SNPs is 15, there are tens of thousands of possible SNP combinations: a very large number of 2-locus systems, numerous 3-locus systems, fewer 4-locus systems, etc., all the way to one 15 locus system. In one embodiment, the software tests each and every possible haplotype system. Haplotype systems are picked lexigraphically using a random number generator, genotype and phenotype data retrieved, haplotypes inferred, inferred haplotypes merged with the phenotype data, patients partitioned into responder and non-responder groups and three different statistical tests are performed to determine whether the patient groups are distinct from one another with respect to their haplotype sequences. Then a second system is picked lexigraphically and treated the same, then a third, and so on until all of the systems have been analyzed. For the 15 SNP gene, the process takes several weeks running on a Sun Enterprise 420R server; completing just the list of possible 3-locus haplotypes takes about 1 week of 24 hour per day computation. The feature extraction system may utilize artificial intelligence algorithms (described later) by which to arrive at the optimal haplotype system in the most expedient manner possible.

Example: TAXOL™ response in Ovarian Cancer patients. In this example, the trait analyzed is the patient response or non-response to a commonly used anti-cancer drug called TAXOL™. TAXOL™ is a registered trademark of the Bristol-Myers Squibb Company. A gene that is suspected to be involved in the disposition of TAXOL™ in the human body, namely CYP3A4, is selected based on suitable predetermined criteria. This criteria may include, e.g., the chemical structure of the drug as well as the body of literature on TAXOL™ metabolism. In this example, the CYP3A4 gene has eight SNPs. Several ovarian cancer patients are genotyped at each one of these SNPs. It is assumed that variants of this gene cause an inability to respond to this particular anti-cancer drug. Since it is not known which or how many SNPs are involved, all possible SNP combinations are tested to find any statistical association for non-response.

In FIG. 8, data regarding CYP3A4 polymorphisms tested for association with TAXOL™ response in Ovarian Cancer patients are shown. The name of the SNP is shown in Column 1 ("SNPNAME"), its unique identifier in Column 2 ("MARKER"), and its location ("LOCATION") in Column 3 within an NCBI reference sequence in Column 4 ("GENBANK"). Its status (whether or not it is a validated polymorphic marker, indicated by "POLY") is in Column 5 ("INTEGRITY"), and the type of polymorphism (whether it is located in a coding, silent, or intron region of the gene) in Column 6 ("TYPE"). The haplotype system described in the text is a combination of the three SNPs named in rows 2, 3, and 8.

The job is defined using, for example, the command structure and data shown below:
QUERYNAME=TX3A1117
GENE=CYP3A4
DRUG=TAXOL
SAMPLEID=ALL
MARKER=809114|664803|712037|869772
TEST=CA125
TRAITS=HAIR|EYE
HAPLOCONTROL=CAN|ANA For the drug and test, TAXOL™ and CA125 (a biochemical measure for tumor size) are entered. For biographical variables, which may represent undesirable covariates, hair and eye color are entered. Race is a common entry here. These data are retrieved in the same way for each cycle of haplotype selection and analysis which follows.

The first of several hundred possible haplotype systems for this gene having eight SNPs is selected for analysis. A single combination of SNP markers from the list in FIG. 8 is selected:
809114 664803 712037 869772

This haplotype system is given a unique name:
TX3A41119

The task is to analyze whether this combination of markers harbor SNP alleles that offer predictive value regarding how a patient responds to TAXOL™.

The program generates an HTML output file for visual inspection, a portion of which is shown in FIGS. 9A–9B for illustration. For each patient, data regarding SAMPLE ID, DRUG, and a prescription START and STOP DATE, along with the corresponding clinical test measurements, are included and displayed. The test measurements in this case are CA125 readings before and after the prescription date. The file data shown is abridged since it is too lengthy to illustrate in its entirety; it refers only to SAMPLE ID of DNAP00118, DNAP00119, and DNAP00120 (first entry only), and only to responders. For the SNPs selected, the patient's genotype is also listed. One could go through the entire HTML file by eye and identify any simple genetic relationships. For example, if every person who displayed an increase in CA125 reading had an "AA" for SNP 809114, it would be easy to visually identify this. Unfortunately, however, human genetic relationships are rarely this straightforward.

The program then generates a text file with the genotypes of each patient. A portion of this text file for the SAMPLE IDs of DNAP00118, DNAP0119, and DNAP00120 (first entry only) is shown below:

DNAP00118

AGGC

ATAC

DNAP00118

AGGC

ATAC

DNAP00118

AGGC

ATAC

DNAP00118

AGGC

ATAC

```
-continued
#DNAP00118

AGGC

ATAC

DNAP00118

AGGC

ATAC

DNAP00118

AGGC

ATAC

#DNAP00119

ATGC

ATAC

#DNAP00119

ATGC

ATAC

#DNAP00119

ATGC

ATAC

#DNAP00119

ATGC

ATAC

#DNAP00119

ATGC

ATAC

#DNAP00120

ATGC

ATAC

.
.
.
```

As shown above, the first patient on the list is:
DNAP00118
AGGC
ATAC

It is known that this particular patient has two four-locus haplotypes, but the phase of the SNP alleles for these haplotypes are unknown. For example, is this patient AGGC/ATAC or AGAC/ATGC? A haplotype inference calculator is therefore used to determine the phase of genotypes for each one of the patients. A portion of the output of this program is shown below:

```
QUERYNAME=TX3A1117

#DNAP00118: (1, 2)

AGAC

ATGC

#DNAP00119: (2, 3)

ATGC

ATAC

#DNAP00120: (2, 3)

ATGC

ATAC

.
.
.
```

From the above, it can be seen that the first patient indeed harbored the AGAC/ATGC pair of haplotypes:
DNAP00118: (1, 2)
AGAC
ATGC The list of phase-known haplotype pairs is then merged with the HTML file to replace the phase-unknown genotypes with the phase-known haplotype pairs. The result is shown (in part) in FIG. 10, which visually appears very similar to FIGS. 9A–9B except that haplotype pairs rather than genotypes are included and displayed.

Having reached this point, the program then partitions the patient data into affected/non-affected groups (in this example, responder and non-responder groups) which is stored in a text file. Since the user has indicated that, for this particular job, the grouping is performed based on a 50% decrease in CA125 readings. In FIG. 11, partitioned data 1102 of cancer patients are shown for illustration, represented by their diploid pair of haplotypes for an arbitrarily selected 4-locus haplotype system based on their response to TAXOL™. Pairs are named H1, H2, etc, and the counts for each pair are shown in column 2. The nucleotide sequence of the pair is shown in the last column, and each nuclotide allele for the SNPs are removed from one another by a blank space. Responders (based on the 50% response criteria) are shown as the top group 1104, and non-responders are shown as the bottom group 1106.

By eye, one can notice in FIG. 11 that a T allele for SNP2 and a T allele for SNP4 are more frequent in the non-responder group than in the responder group. However, a more objective way to identify whether alleles of this haplotype system are predictive of response is to use a statistical test. When the 50% reduction in CA125 level is used as the criteria separating responders from non-responders, it can be concluded that the TX3A41119 haplotype constituency between the two groups is different with a $p<0.00000+-0.0000$, using the FST P value test (Generally, a $p<0.05$ is viewed as an indication of statistical certainty). Other ways of partitioning the patient data can reveal similar results for the TX3A41119 haplotype system. As examples, using a 20% criteria, considering average readings per patient instead of each reading each patient on its own, or using a different statistical test, etc. Thereafter, the process is repeated to test additional haplotype systems. A second haplotype system is processed, then a third, etc., until all possible haplotypes have been processed.

In FIG. 12, data 1202 regarding differentiation tests of genetic structure between paclitaxel responders and non-responders with Ovarian Cancer are shown. Analyses for haplotype systems (Column 2) within two genes (Column 1) are presented. Two criteria for response were used: a 20% and a 50% reduction in CA125 reading post-paclitaxel treatment. The analyses were performed on two levels (Column 4). The "individual level" uses an average CA125 response per individual and counts each individual only once. The "test pair" level uses each paclitaxel treatment—CA125 reading pair, and any one individual may be counted several times depending on the number of treatments they received. P values for a pair-wise F-statistic (Column 4) and an Exact test of Differentiation (Column 5) are shown. In FIG. 12, the results from the first two haplotype systems processed can be compared. This reveals that the second haplotype system (TX3A41120) revealed poor P-values, no matter how the data was looked at.

After having screened through thousands of haplotype systems, in this and other genes, the TX3A41119 system proved to be the optimal system for genetically distinguishing between TAXOL™ responders and non-responders. The program took about one week to run for this example, but if done by hand it is estimated that the process would have taken a year or more. If the longest possible haplotype had been focused on, the contribution of the three most important SNPs would have been missed (those SNPs that comprise the TX3A41119 haplotype system because of the confounding affect of irrelevant SNPs and because of dilution of the sample size within each genetic class).

The final output of the program is the definition of the optimal haplotype system, its qualifying statistics, and the DNA sequence information of its constituent SNPs. See FIG. 13, which shows data 1302 regarding the polymorphisms comprising the optimal haplotype system for predicting TAXOL™ response. Only the first SNP of the three is shown. The name of the SNP (SNPNAME), its unique identifier (MARKER), location within a genbank reference sequence (LOCATION, GENBANK) and validation status (INTEGRITY) are shown along with the type of polymorphism (SILENT). The sequence immediately five prime to the SNP is shown (FIVEPRIME), the SNP position follows the last sequence of this five prime sequence and is indicated with an IUB code under VARIANT. The sequence immediately flanking the SNP to its 3' side is shown under THREEPRIME.

Although mutations and SNPs in the CYP3A gene have been shown by others to contribute towards variable response to other drugs, until this result was obtained, it was not known whether or how common polymorphisms in this gene were related to variable paclitaxel response. Thus, a classifier that could be developed as a result of this successful application could be used by oncologists to match ovarian cancer patients with the optimal dose and drug for chemotherapy most appropriate for their genetic constitution.

Efficient Algorithms. Because the number of haplotype systems can be quite large for even relatively small sets of SNPs, alternate embodiments allow for the reduction of the work required in identifying the optimal set of markers associated with a genetic trait. A preferred method of performing this screening of haplotype systems is to focus on 3-locus haplotype systems first, and thereafter focus on the minimal set of markers that could be used to explain the trait. Using additional algorithms, the dimensionality of the haplotype system screen is expanded (4-, 5-, 6-locus, etc.) or reduced (2-locus). Although it is preferred to initially analyze a 3-locus haplotype system, any suitable numbered locus system may be used to begin.

Consider a 3-locus screen, which for a collection of 15 SNPs (for example) includes about 450 possible 3-SNP combinations. If each and every possible N-locus combination were screened, there would be about 10,000 haplotype systems, which would take weeks for analysis. In this embodiment, however, the results of the 3-locus analysis are used to determine which 1-, 2-, 4-, 5-, 6-, . . . , n-locus haplotype systems are likely to be associated with the trait Once found, the limited number of haplotype systems are screened much more rapidly and the best one of all n-locus haplotype systems screened is selected.

The software may alternatively process 2-locus haplotypes initially rather than 3-locus haplotypes to achieve better efficiency. For any N-SNP gene, the number of 2-locus haplotypes is smaller $[(N)(N-1)/2]$ than the number of 3-locus haplotype systems $[(N)(N-1)(N-2)/(3*2)]$. Therefore, there are fewer haplotype inferences and statistical analyses for 2-locus haplotypes. However, the potential downside is that more complex and informative associations may be concealed at the expense of this computational efficiency. Fortunately, the intelligent processing of the present invention described above ameliorates this concern.

The present method identifies N-locus haplotype pairs associated with a trait, and the intelligent processing utilizes a novel statistical method to identify the most important SNPs within these N-locus haplotypes. Together, these constitute a haplotype system or a system of all alleles of a given multilocus genotype collection. After identifying which SNPs contribute most towards the significance of association, a list of these SNPs are constructed. Only those higher-order haplotype systems that contain these SNPs are tested, thereby saving tremendous amounts of processing time and memory. In fact, since the claimed method allows for an intelligent selection of higher-order haplotype systems, it is technically superior to begin with a 2-locus survey and graduate to select 3, 4, . . . , N-loci surveys. Doing so maximizes the efficiency of resource use without sacrificing sensitivity.

Consider the following actual test which utilized a single SUN 420R server and began with a 3-locus search. There were 14 SNPs in a particular gene, and it was to be determined whether and which haplotype alleles were associated with a particular trait. A single collection of 4 SNPs form alleles that optimally resolve between trait values exists.

Beginning with the 3-locus combinations, genotype data, phenotype data, and inferred haplotypes for $(14*13*12)/(3*2)$ SNP combinations=364 must be obtained. Each combination takes about 10 minutes for data retrieval, 1 hour to infer haplotypes, 10 minutes to prepare output and input files, and 10 minutes for statistical analysis. For 364 combinations, 32,760 minutes were spent performing the analysis. Significant results were obtained and 5 SNP combinations whose haplotype alleles are associated with the trait were identified. The intelligence method identified 8 SNPs that contributed most towards this significance, and $(8*7*6*5)/(4*3*2)=70$ 4-SNP combinations (rather than $(14*13*12*11)/(4*3*2)=1001$ without the intelligence method) were tested and then $(8*7*6*5*4)/(5*4*3*2)=56$ 5-SNP combinations (rather than $(14*13*12*11*10)/(5*4*3*2)=2002$ without the intelligence method) were tested. This adds another (90 minutes*70)+(90 minutes*56)=11340 minutes for a combined run time of 32,760+11340=44,100 minutes or 735 hours to find the 4-locus combination.

Using the single SUN 420R server with an initial 2-locus search provides for better efficiency. Beginning with 2-locus combinations, genotype data, phenotype data, and inferred haplotypes for (14*13)/(2) SNP combinations=91 must be obtained. Each combination took about 10 minutes for data retrieval, 1 hour to infer haplotypes, 10 minutes to prepare output and input files, and 10 minutes for statistical analysis (same as above). For 91 combinations, 8190 minutes were spent performing this analysis. Significant results were obtained and 9 SNP combinations whose haplotype alleles are associated with the trait were identified. The intelligence method identified the same 8 SNPs that contributed most towards this significance, and (8*7*6)/(3*2)=56 3-SNP combinations (rather than (14*13*12*11)/(4*3*2)=1001 without the intelligence method) were tested and then (8*7*6*5)/(4*3*2)=70 4-SNP combinations (rather than (14*13*12*11*10)/(5*4*3*2)=2002 without the intelligence method) were tested, and then (8*7*6*5*4)/(5*4*3*2)=120 5-locus combinations (rather than (14*13*12*11*10)/(5*4*3*2)=2002 without the intelligence method) were tested. This adds another (90 minutes*56)+(90 minutes*70)+(90 minutes*120)=22,140 minutes for a combined run time of 8190+22,140=30,330 minutes or 505 hours to find the same 4-locus combination.

Thus, starting with a 2-locus search rather than a 3-locus search, 230 hours off the compute time have been saved. The same, most likely "features" associated with the trait have been screened using both the 2- and 3-locus screen, but the 2-locus screen was accomplished in ⅔rds the time. When running the analysis over multiple genes, or in genes with more SNPs, the time savings can be tremendous.

Figure 14:
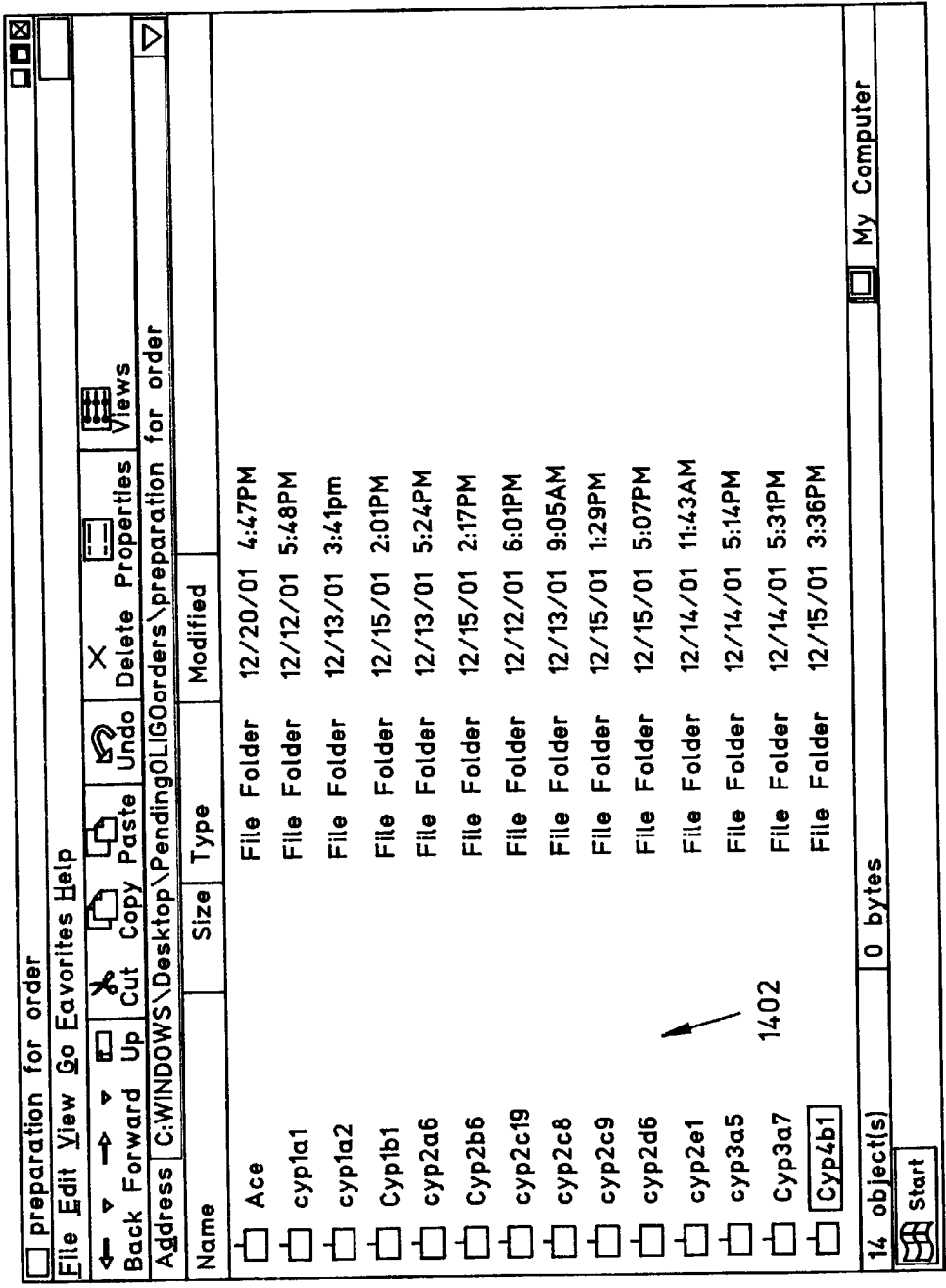

Output Results Navigation. The software also may provide a set of software folders and subfolders containing the results. FIG. 14 shows the output 1400 of a 14-gene screen for a particular drug reaction trait. A first navigation folder 1404 contains subfolders 1402 in one example output of a software run. Subfolders 1402 contain all of the data for each of the genes. The genes tested are indicated in the name of each subfolder 1402, and within each subfolder 1402 exist all of the data pertaining to the screen for each gene.

Figure 15:
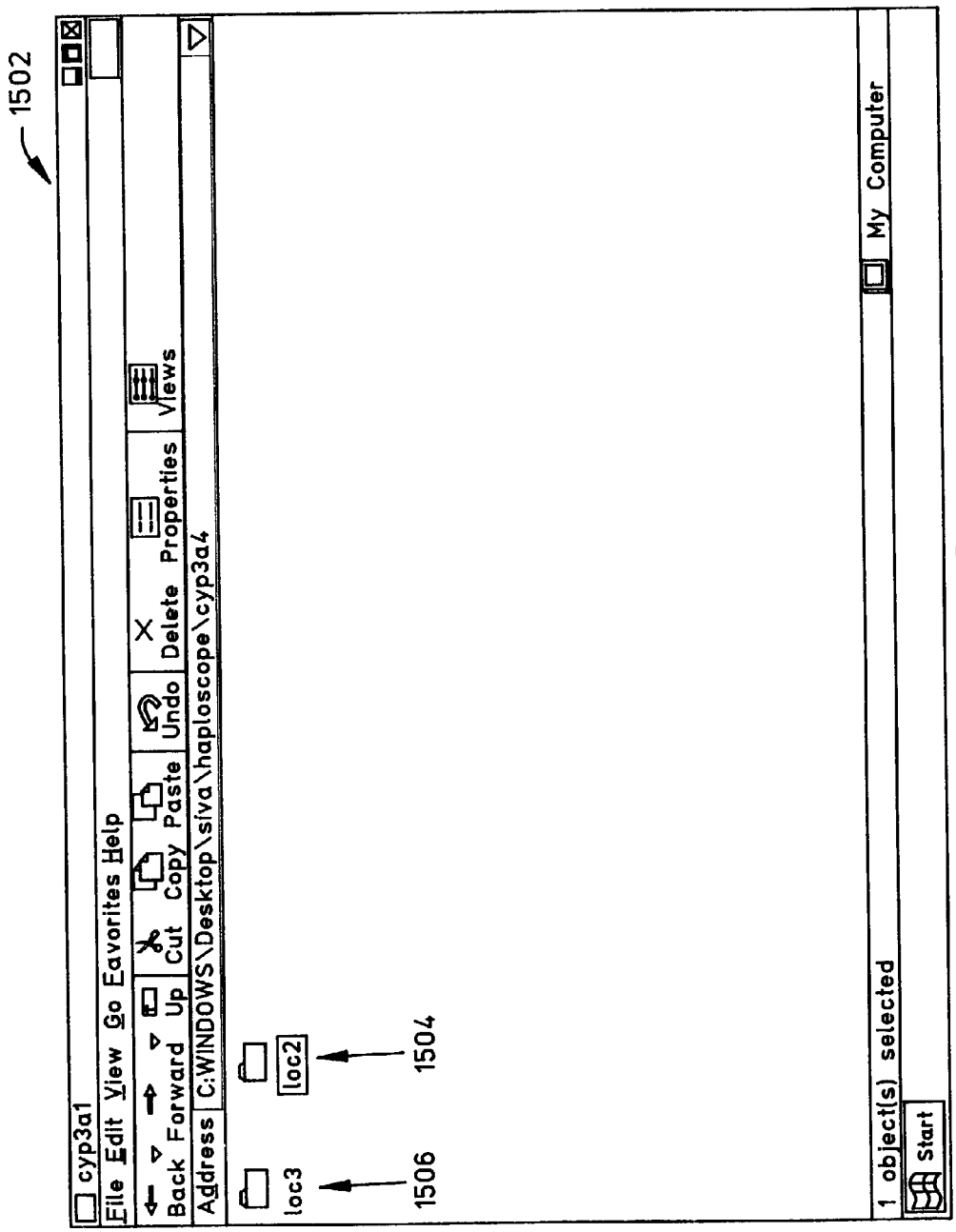

FIG. 15 shows the result when a subfolder 1502 for a gene (in this case, gene "CYP3A4") is opened in FIG. 14. In his example, all 2-locus SNP combinations were tested (results in "loc2" folder 1504) and all 3-locus SNP combinations were tested using the intelligence option (results in "loc3" folder 1506). When a user desires to see the results for the 3-locus screen, the user opens the "loc3" folder 1506 and obtains the output 1600 shown in FIG. 16. All of the data input and output files for the 3-locus analysis of this gene are shown. Files shown are stored in the loc3 subfolder of each gene's analysis folder (in this case, the CYP3A4 gene folder), and each gene folder contains a similar profile of constituents.

Figure 16:
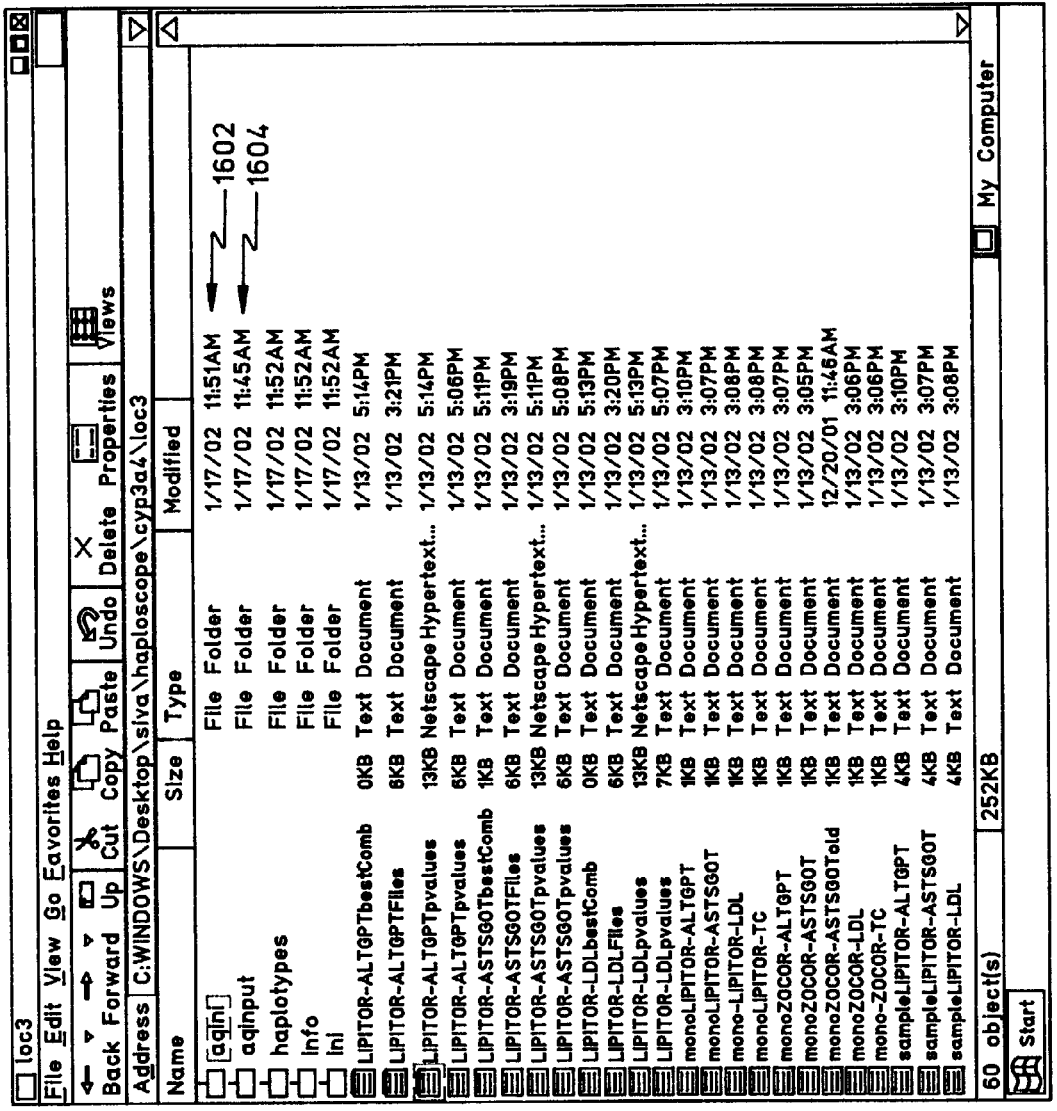
Figure 18:
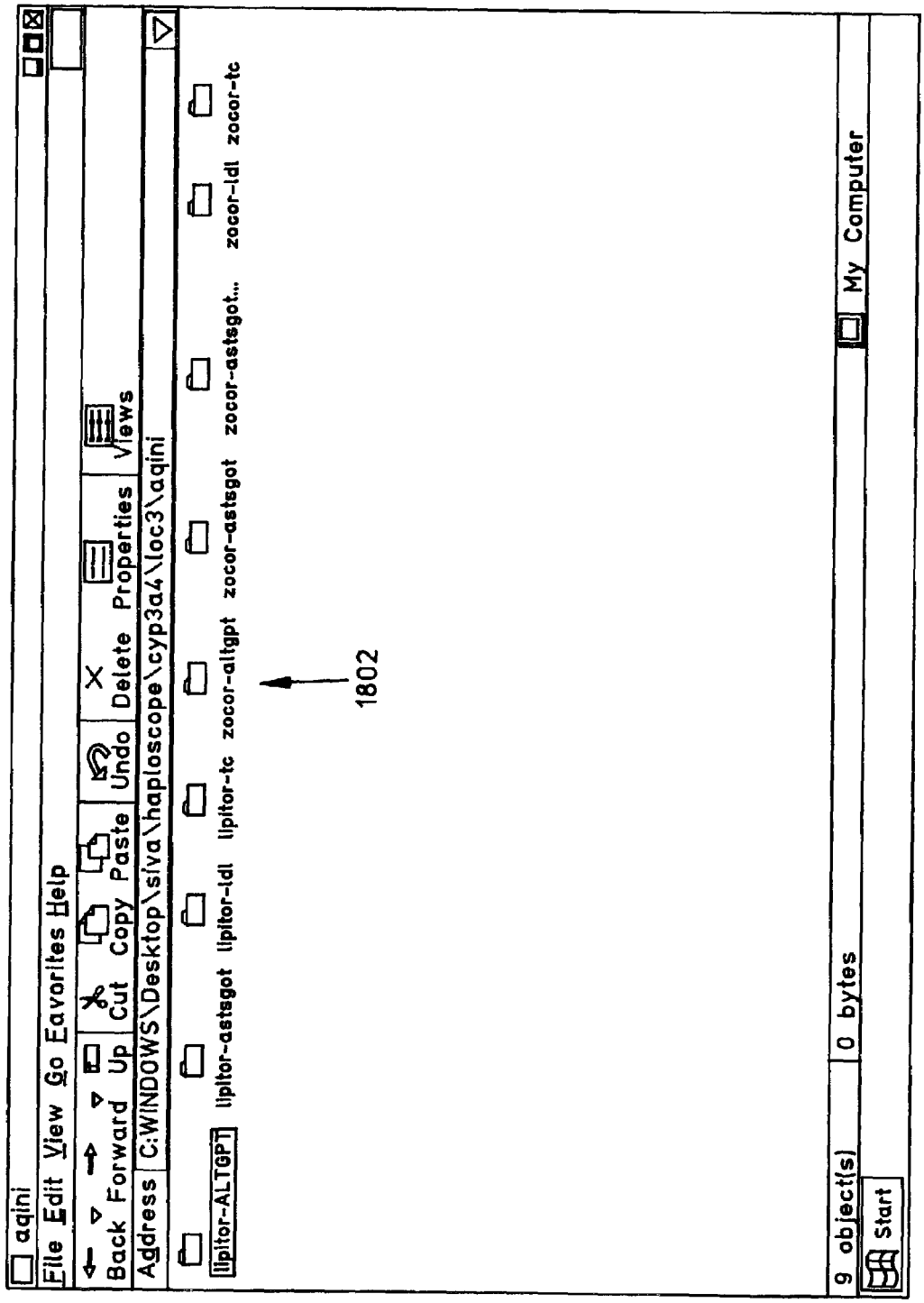

An "aquini" folder 1602 in FIG. 16 contains all of the query files for data retrieval from the (Oracle) database (specifying the drug, clinical test, patient subtype, and SNP marker combination). In this example, queries were run for four different test types (ALTGPT, ASTSGOT, TC, and LDL) that measure the response to two different drugs (Lipitor™ and Zocor™). Note that one was run twice so there are actually 9 folders rather than 8. Opening a folder provides all of the input files by query unique identifier so that the precise query parameters can be seen. These files are used as a batch input for the data retrieval system as well as a record of the queries. In FIG. 18, the "aquini" subfolder 1800 containing all of the unique query folders 1802 is shown. Within each unique query folder exist all of the input files for constructing each query. The programs described operate from these files in batch format.

An "aquinput" folder 1604 in FIG. 16 particularly contains:

1) A "chisquare" folder containing all of the chi-square contingency tables for each query, assembled from the retrieved data in the "aquini" folder 1602. One folder exists for each query type (i.e. Lipitor™ drug and ASTSGOT readings), and each of these folders contains several hundred contingency tables names by query unique identifier plus a suffix to identify them as chi-square input files;

2) A "data" folder containing all of the population substructure analysis input files—one for each query type "*" query. For example, when this folder is opened, a folder for each query type is shown (i.e. Lipitor™ drug and ASTSGOT readings, as one example), and in this folder exist all of the input files for running Fishers and Exact tests of population substructure difference. These text files take the form as shown in the output 1700 in FIG. 17; and 3) A "ready 2 go" folder containing the same material present in the "data" folder, but formatted for input to the F-statistic and Exact test programs. In this example, the Arlequin software package was employed ("A software for population genetic analysis"; Raymond and Rousset, 1997).

The "haplotypes" folder in FIG. 16 contains all of the input and output files used for inferring haplotype phase for each query. When the user opens this folder, two subfolders appear: (1) a "phase2db" folder, which contains all of the input files for the preferred haplotype inference program; and (2) a "phaseoutput" folder which contains all of the output files for the preferred haplotype inference program. In this example, each of these folders contain several hundred files identified by query unique identifier and a suffix to denote their function. The "info" folder in FIG. 16 contains reference data for the queries. The "markercomb" text file within this folder contains a list of all the marker combinations tested and the "uniquesample" text file contains a list of all unique SNP markers incorporated in these combinations. The "phaseinput" folder in FIG. 16 contains two folders—a "rawFiles" folder containing all of the input files for the preferred haplotype inference program and a "uniquefiles" folder containing all of these same text files properly formatted. These files are drawn from by the programs that create the "haplotypes" folder previously described. The "ini" folder in FIG. 16 contains all of the text input files for merging inferred haplotypes with phenotype data formerly retrieved using queries present in the "aquini" folder. The program that merges these two databases is one of the components of the claimed method. The rest of the files in the loc3 folder contain the results.

The file names indicate the type of results contained. For example, the ZOCOR-TCpvalues file contains the following data:

```
CYP3A4LOC3-1214-12  1% UP
CYP3A4LOC3-1214-12  10% UP
CYP3A4LOC3-1214-12  20% UP
CYP3A4LOC3-1214-16  1% UP
CYP3A4LOC3-1214-17  1% UP
CYP3A4LOC3-1214-17  10% UP
CYP3A4LOC3-1214-17  20% UP
CYP3A4LOC3-1214-27  1% UP
```

-continued

| | |
|---|---|
| CYP3A4LOC3-1214-27 | 10% UP |
| CYP3A4LOC3-1214-27 | 20% UP |
| CYP3A4LOC3-1214-3 | 10% UP |
| CYP3A4LOC3-1214-3 | 20% UP |
| CYP3A4LOC3-1214-31 | 1% UP |
| CYP3A4LOC3-1214-31 | 10% UP |
| CYP3A4LOC3-1214-31 | 20% UP |
| CYP3A4LOC3-1214-32 | 1% UP |
| CYP3A4LOC3-1214-32 | 10% UP |
| CYP3A4LOC3-1214-32 | 20% UP |
| CYP3A4LOC3-1214-47 | 1% UP |
| CYP3A4LOC3-1214-48 | 1% UP |
| CYP3A4LQc3-1214-48 | 10% UP |
| CYP3A4LOC3-1214-48 | 20% UP |

This data shows that alleles of several 3-locus SNP combinations were significantly associated with each a 1%, 10%, and 20% response to ZOCOR as measured with the TC test (for example, the CYP3A4LOC3-1214-12 haplotype system). Some of the haplotype systems showed a significant association with only a 10% and 20% response, but not a 1% response. These are considered less than optimally informative SNP combinations and can be discarded. In this example, alleles of 6 different 3-locus combinations were associated with TC response in ZOCOR patients.

HTML files which show each patients response are also included. Examples of these files were shown in other parts of this application. The HTML files allow for a visual inspection of specific results learned from the other output files.

Files that begin with the word "sample . . . " contain a listing of the sample size for each query. For example, the following text from one of these files shows that the sample sizes varied slightly from query to query (due to missing genotype data for some SNP markers in some individuals):

| | |
|---|---|
| CYP3A4LOC3-1214-25 | 108 |
| CYP3A4LOC3-1214-25 | 108 |
| CYP3A4LOC3-1214-26 | 112 |
| CYP3A4LOC3-1214-26 | 112 |
| CYP3A4LOC3-1214-26 | 112 |
| CYP3A4LOC3-1214-27 | 108 |
| CYP3A4LOC3-1214-27 | 108 |
| CYP3A4LOC3-1214-27 | 108 |
| CYP3A4LOC3-1214-28 | 110 |
| CYP3A4LOC3-1214-28 | 110 |
| CYP3A4LOC3-1214-28 | 110 |
| CYPJA4LQC3-1214-29 | 108 |

-continued

| | |
|---|---|
| CYP3A4LOC3-1214-29 | 108 |
| CYP3A4LOC3-1214-29 | 108 |
| CYP3A4LOC3-1214-2 | 110 |

Files beginning with the word "mono . . . " contain a listing of all the queries that were dumped because of inadequate polymorphism for comparison (i.e. all three markers were monomorphic in the specific subset of patients taking a particular drug and having no missing data for a particular test type). These files serve as references only.

Other Advanced Techniques. Using the results for the 3-locus haplotype system screen, the techniques performed for each practice are: (1) a simultaneous testing procedure for screening lower order (e.g. 1- or 2-locus) haplotype systems; and (2) a directed haplotype system expansion algorithm to select and screen higher-order (e.g. greater than 3-locus) haplotype systems.

Simultaneous Testing Procedure. A simultaneous testing procedure (STP) is used to reduce the dimensionality of a haplotype system screen. This procedure is performed by what is referred to as an STP processor in computer device 112 of FIG. 3. The goal of the procedure is to determine whether a subset of the optimal 3-locus haplotype system(s) can be used to explain the trait association. In particular, the new statistical method is used to determine the minimum set of rows in a Row by Column (R×C) contingency table of discrete data that explains the dependence of observations.

Interpretation of categorical data through two-way R×C contingency table analysis is in practice in many areas of quantitative studies. Most often, however, analysis is limited to inference of independence/dependence of rows (R) and columns (C). The aim here is to provide software code for determining which rows (R) and/or columns (C) are the source of dependence observed in a specific set of data. This problem is studied by examining the following aims: (1) determination of a suitable decomposition of the total chi-square from a R×C contingency table that allows testing which sets of rows or columns explain the dependence in the total data; and (2) developing a stepwise procedure to determine the minimum set of rows and/or columns that explains the dependence.

First it is tested whether the two multinomial population distributions ($P(p_1, p_2, p_3, \ldots, p_k)$ and $Q(q_1, q_2, \ldots, q_k)$) are statistically the same. This is similar to testing the null hypothesis $$H_o: p_i = q_i \text{ for } i=1, 2, \ldots, k \quad (1)$$

against $$H_A: p_i \neq q_i \text{ for at least one } I=1, 2, \ldots, k \quad (2)$$

Rejection of null hypothesis ($H_o$) by itself does not address the question of which cells, or how many of them, differ in frequencies in the populations. However, STP address the following questions: (1) What is the minimum set of cells with respect to each of which $p_i \neq q_i$ and (2) What is the minimum threshold cell probability for the set of cells with respect to which the two populations do not differ significantly for each other.

A review of analysis techniques for subtables in the R×C contingency table is provided. Various techniques to decompose an R×C contingency table are available in the literature. Goodman (1979) and Freeman (1987) point out that there are three major approaches for this purpose. One approach is to check the specific contribution to a chi-square statistic of each cell, or each row, or each column, depending on different situations. In the simple case of comparing two populations, if the criterion of one degree of freedom and a 5% level of significance is used, then the large values of cells will exceed 3.83. On this basis of the contribution to a chi-square, the cells with values over 3.84 differ significantly from what would be expected from a homogeneous population. A second approach is to examine standardized residuals. These are defined as $Z_{ij}=(n_{ij}-m_{ij})/\sqrt{m_{ij}}$ is a standard normal variable. This method is almost the same as the above. Everitt (1977), Freeman (1987) and Agresti (1990) have discussed this method in detail.

A third approach is the decomposition of a chi-square. The basic feature is to partition an R×C contingency table into more interpretable sub tables, from which the components of a chi-square statistics are calculated. For decomposition of a chi-square, the following rules should be followed: (1) the number of subtables cannot be greater than the degrees of freedom of the test statistic for the original table; (2) each cell frequency of the original table must appear as cell frequency in one and only one sub table; (3) each marginal total of the original table must appear as a marginal total of one and only one subtable; and (4) subtable cell frequencies not appearing in the original table must appear as marginal totals in different subtables. Marginal totals not appearing in the original must appear as either cell or grand totals.

Several techniques for the analysis of subtables are provided. Lancaster (1949) and Irwin (1949) have shown that the overall chi-square statistic for R×C contingency table can always be partitioned into as many components as they have one degree of freedom. Each component chi-square value corresponds to a particular 2×2 table arising from the original table, and each component is independent of the other. Gabriel (1966, 1969) proposed a simultaneous method to test homogeneity across multiple subtables of an R×C contingency table. Finally, George (1997) proposed an STP that ameliorates the difficulties in earlier methods.

A significant overall chi-square test for an R×C contingency table indicates differences among the proportions across populations, but provides no information as to whether these differences occur throughout or in a specific part of the table. Therefore, one would prefer to make additional comparisons of cells within the whole table. Once the full null hypothesis is rejected, the basic feature of the method is the decomposition of $\chi^2$ and simultaneously testing for several homogeneity hypotheses. In order to find those specific bins which include different frequencies among populations under rejecting the full null hypothesis, the whole space is divided into two mutually exclusive subsets. One is called $S_1$ and the other is called $S_2$. In the simplest case, there are two populations and their probability functions on $\Omega$ are $P(p_1, p_2, p_3, \ldots, p_k)$ and $Q(q_1, q_2, \ldots q_k)$, respectively. Two sets $S_1$ and $S_2$ are obvious choice of target sets when they satisfy the following properties:

1. $\Omega = S_1 \cup S_2$
2. in $S_1$, $p_i \neq q_i$, (i=1, 2, ..., $s_1$, and $p_i \subset P$; and $q_i \subset Q$)
3. in $S_2$, $p_j = q_j$ (j=1, 2, ..., $s_2$, and and $p_j \subset P$; and $q_j \subset Q$)
4. $S_1 \cap S_2 = \phi$
5. $s_1 + s_2 = K$ (K is the ≠of comparable bins.)

Clearly, $S_1$ includes all specific categories in which $p_i \neq q_i$, and $S_2$ in which all $p_j = q_j$.

First, according to the extent of the contribution of each category ($C_i$) to the $\chi^2$ in the overall homogeneity test, they can be rearranged from large to small. Suppose that the sets $\{C_i\}$ arranged in order are denoted by $C_{(1)}, C_{(2)}, \ldots, C_{(k)}$. As mentioned above, $S_1$ in which $p_i \neq q_i$ should include those categories with larger contribution to the $\chi^2$ value; and $S_2$ in which $p_j = q_j$ should include those with smaller contribution values to $\chi^2$. Depending on the corresponding chi-square values of these categories, some value can be used such as 3.84 in R×2 tables as a standard and divide categories into two subsets, call them $U^{(0)}$ and $V^{(0)}$.

Let $U^{(0)} = \{C_{(1)}, C_{(2)}, \ldots, C_{(L)}\}$ and $V^{(0)} = \{C_{(L+1)}, C_{(L+2)}, \ldots, C_{(K)}\}$, whole table is also divided into two parts with $U^{(0)}$ and $V^{(0)}$:

| Part 1: $U^{(0)}$ | | | |
|---|---|---|---|
| $C_{(1)}$ | $n_{(11)}$ | $n_{(12)}$ | $n_{(1.)}$ |
| $C_{(2)}$ | $n_{(21)}$ | $n_{(22)}$ | $n_{(2.)}$ |
| ... | ... | ... | ... |
| $C_{(L)}$ | $n_{(L1)}$ | $n_{(L2)}$ | $n_{(L.)}$ |
| | $t_{(11)}$ | $t_{(12)}$ | $n_{1.}$ |
| Part 2: $V^{(0)}$ | | | |
| $C_{(L+1)}$ | $n_{(L+1,1)}$ | $n_{(L+1,2)}$ | $n_{(L+1.)}$ |
| $C_{(L+2)}$ | $n_{(L+2,1)}$ | $n_{(L+2,2)}$ | $n_{(L+2.)}$ |
| ... | ... | ... | ... |
| $C_{(K)}$ | $n_{(K1)}$ | $n_{(K2)}$ | $n_{(K)}$ |
| | $t_{(21)}$ | $t_{(22)}$ | $n_{(2)}$ |

In addition, an extra table needs to be constructed that includes column marginal totals, defined as $\{M^{(0)}|U^{(0)}, V^{(0)}\}$ as follows:

| | | | |
|---|---|---|---|
| Part1 | $t_{(11)}$ | $t_{(12)}$ | $n_{(1.)}$ |
| Part2 | $t_{(21)}$ | $t_{(22)}$ | $n_{(2.)}$ |
| | $t_{(.1)}$ | $t(.2)$ | n |

At this junction, the tow partial and marginal homogeneity hypothesis needs to be tested: $H^{(0)}_{01}$ for subset $U^{(0)}$; $H^{(0)}_{02}$ for subset $V^{(0)}$; and $H^{(0)}_{0m}$ for their column marginal set $\{M^{(0)}|U^{(0)}, V^{(0)}\}$. Let $H_0(\Omega)$ be the full homogeneity hypothesis, then the relation among these homogeneity hypothesis can be written as:

$H_0(\Omega) = H_{01} \cap H_{02} \cap H_{0m}$.

This is because, if $H_0(\Omega)$ holds for all i=1,2, ..., k, then $p_j = q_j$ must also hold.

In this procedure, it is clear that if $H_{01}(S_1)$ is rejected and $H_{02}(S_2)$ and $H_{0M}(M|S_1, S_2)$ is simultaneously rejected. Under rejecting the full homogeneity $H_0(\Omega)$, then the target subsets $S_1$ and $S_2$ can be found. In $S_1$, all the categories with different $p_i$ and $q_i$; in $S_2$, all the $p_j$ and $q_j$ are the same.

The problem of selecting a significance level ($\alpha$) for testing n statistically independent tests is discussed by various authors. For detailed discussion about this problem, one may refer to Fisher (1933), Brunden (1972), Everitt (1977), Weir (1992), and Chakraboty (1994). Here we use a Bomferroni inequality test for multiple comparison procedures. If the number of comparison tests is n, and the total significance level is α, then the significance test for each test is $α_i=α/3$ for i=1, 2, . . . , n.

Example. In the study of the association between genotypes and eye color, Table 1 is constructed for OCA3LOC109 gene.

TABLE 1

| Genotype/Eye Color | Light | Dark | Total |
|---|---|---|---|
| G11: (ATA, ATA) | 47 | 11 | 58 |
| G12: (ATA, ATG) | 55 | 10 | 65 |
| G13: (ATA, ACG) | 1 | 0 | 1 |
| G14: (ATA, GCA) | 29 | 7 | 36 |
| G15: (ATA, GCG) | 16 | 6 | 22 |
| G16: (ATA, GTA) | 3 | 4 | 7 |
| G17: (ATA, GTG) | 3 | 4 | 7 |
| G22: (ATG, ATG) | 16 | 6 | 22 |
| G23: (ATG, ACG) | 1 | 0 | 1 |
| G24: (ATG, GCA) | 8 | 8 | 16 |
| G25: (ATG, GCG) | 10 | 10 | 20 |
| G26: (ATG, GTA) | 0 | 1 | 1 |
| G27: (ATG, GTG) | 0 | 2 | 2 |
| G44: (GCA, GCA) | 5 | 6 | 11 |
| G45: (GCA, GCG) | 3 | 4 | 7 |
| G47: (GCA, GTG) | 1 | 0 | 1 |
| G55: (GCG, GCG) | 1 | 2 | 3 |
| G56: (GCG, GTA) | 0 | 1 | 1 |
| Total | 199 | 82 | 281 |

The Chi-square value=42.5478. Under the significant level of 0.05, when the degree of freedom is 17, the critical value of $χ^2$ is 32.2020. So, the null hypothesis $H_0(Ω)$ needs to be rejected. Then some specific genotypes are chosen based on the above table, which explain this significance.

If using 3.0 as standard, the whole table of 18 rows can be divided into two subsets: $U^0$={G12, G24, G25, G27, G44} and $V^0$={G11, G13, G14, G15, G16, G17, G22, G23, G26, G45, G47, G55, G56}. The null hypothesis is tested for the two subsets and their column marginal set W. The results of stepwise of STP are shown in Table 2 below:

TABLE 2

| Subset | $χ^2$ Value | Degrees of Freedom | Critical $χ^2$ value |
|---|---|---|---|
| $U^0$ | 20.5620 | 4 | 9.49 |
| $V^0$ | 21.2442 | 12 | 21.03 |
| $W^0$ | 0.5335 | 1 | 3.84 |

As apparent, the subset of genotypes $U^0$, but not $V^0$ or $W^0$, have a chi-square value that exceeds the critical chi-square value, and it therefore is statistically significant. Thus, the relevant contributors to the significant chi-square value are decomposed to the subset of genotypes $U^0$, which explain most of the significance in the original table.

A statistical method to reduce the n-dimensional order of the optimal haplotype system for explaining the variance of a given trait has just been described. If a particular 3-locus haplotype system explains a trait well, but only because the second and third SNPs of the haplotype system are useful (and not the first), for example, the above method will identify this situation. However, there could be numerous 3-locus haplotype systems because there are numerous markers associated with the trait. If there are eight haplotype systems with three unique SNPs associated with a trait, it is possible that there is a 4-, 5-, 6-, 7-, or 8-locus haplotype system that could be even more tightly associated with the trait. However, testing all of the possible 4-, 5-, 6-, 7- and 8-locus haplotype systems would involve screening thousands of haplotyps systems.

Therefore, another approach is to direct the search, utilizing the results of the 3-locus haplotype system screen, to include only the higher order haplotype systems that are likely to be associated with the trait. This method of testing higher order haplotype systems in a manner which conserves computational time and resources is called the Directed Haplotype System Expansion Algorithm (DHSEA). This process is performed by what is referred to as a directed search processor in computer device 112 of FIG. 3. An F-statistic p-value and a Fishers Exact p value is used to judge each haplotype system. One, two, or three trait criteria for which to calculate these two p-values may be used (for example, a 10% response to a drug and a 20% response to a drug).

Assume that a 3-locus haplotype system screen has been completed, where 10 interesting candidates that are associated with both a 10% and 20% response to a drug have been identified. The method first involves ranking the 3-locus systems based on the sum of p-values. All haplotype systems part of this list will have the same number of p-values to add. If the sample size of a given haplotype system is low with respect to the average, a penalty is assigned to the sum. Next, the sums are divided by the number of p-values calculated for each haplotype system. A list of haplotype systems whose average p-values are below 0.05 is then created. From this list, a list of the unique SNP markers is also generated. From this subset of SNP markers, all possible n-dimensional haplotype systems where n>3 are defined and screened. Next, a list of all n-dimensional haplotype systems with an average p-value<0.05 is created, and these are ranked in descending order for visual inspection by a user.

Thus, this process effectively "directs" a search for the best haplotype system by using what has been learned from the screen of all possible 3-locus SNP combinations to define the larger haplotype systems that are most likely to be associated with a trait. The process can be further directed by considering the number of times a SNP marker is present in the set of significant haplotype systems. Those that are present frequently could be given a preference and haplotype systems incorporating them could be tested first, or only these haplotype systems could be tested, depending on the amount of time available (see below).

Assume that five haplotype systems with significant average p-values have been identified:

| | | |
|---|---|---|
| 1. | Sample size = 199 | 554363\|554368\|869785 |
| 2. | Sample size = 181 | 554363\|554366\|554368 |

-continued

| 3. | Sample size = 190 | 554363\|554366\|869785 |
| 4. | Sample size = 214 | 554363\|756250\|869785 |
| 5. | Sample size = 103 | 554360\|554365\|869785 |

From this list, a list of the unique SNP markers is generated, with the number of times each appears in the haplotype list in parenthesis:

| 1. | 554363 | (5) |
| 2. | 869785 | (4) |
| 3. | 554368 | (2) |
| 4. | 554366 | (2) |
| 5. | 554360 | (1) |

There are a very large number of possible 4-, 5-, 6-, . . . , n-locus haplotype systems that could be tested from the original collection of markers. However, the results show that the above five markers are consistently present in valuable 3-locus haplotype systems. Therefore, the screen is directed towards 4-, 5-, 6-, . . . , n-locus haplotype systems that incorporate these markers. The number of tests is thus dramatically reduced, saving computational time and resources.

Complex Genetics Modeling. The overall method described thus far has been a "feature extraction" method. A feature is an attribute that can be used to distinguish individuals from one another. Visually useful features such as nose shape, hair color and height are obvious to the lay person, but geneticists strive to identify "genetic features" (sequences, haplotypes etc.) that distinguish between clinically relevant traits (such as disease status or drug response). Haplotype systems are "genetic features" in that they can be used to an extent to distinguish among individuals and groups of individuals. This term has been coined to represent haplotype systems as component pieces of a given complex genetics puzzle (i.e. a typical human trait).

Thus, the method described above is a novel method for identifying the best haplotype system features for a given trait. However, clinically important traits are often times caused by several genes interacting together (i.e. they are complex), and the identification of optimal features within individual genes is the first step in developing a genetic "solution" for a trait. For example, assume a trait is caused by certain haplotypes in four different genes. Having identified the optimal haplotype systems within each gene, the question then becomes how they work together to cause the trait. This is a mathematically demanding area of genetic research that is just now becoming recognized as crucial for the application of genomics technology for clinical advances, and advance in the field is beginning to come from hard scientists with training in mathematics, engineering and physics rather than molecular biology or genetics.

A method for assembling genetic (haplotype system) features into a complex genetic model is now described. This is subsequent process is important for developing classification tests, and is performed by what is referred to as a statistical modeling processor in computer device 112 of FIG. 3. The modeling technique described below are linear and quadratic techniques, although other suitable techniques may be utilized. For example, a correspondence analysis or a classification tree method may be used as described in Provisional Application Serial No. 60/338,771 filed Dec. 3, 2001.

Linear Classification procedure for Complex Traits: Human Eye Colors as an Example. The pooled within-population variance-covariance matrix can be computed from $$S = \sum p_{i=1} \sum N_{i\,j=1}(Y_{ij} - \mu_i)(Y_{ij} - \mu_i)'/\sum (N_i - 1) \quad (1)$$

where $Y_{ij}$ is the vector of character measurements for the j'th individual in the i'th trait value. $\mu_i$ and $N_i$ are the vector of means and sample size for the i'th trait value.

The generalized distance of the ij'th individual form the mean of the k'th trait value can be computed from $$D^2_{ij,k} = (Y_{ij} - \mu_k)' S^{-1}(Y_{ij} - \mu_k) \text{ for } k \neq I \quad (2)$$

The vector $Y_{ij}$ is used to calculate $\mu_k$, the mean of its own eye color. To avoid circularity caused by this, Smouse (1976) used correction when comparing an individual with the mean of its own eye color:

$$D^2_{ij,i} = (N_i/(N_i-1))^2 (Y_{ij}-\mu_i)' S^{-1}(Y_{ij}-\mu_i) \quad (3)$$

The usual procedure is to allocate the ij'th individual to that trait value for which (2)/(3) is minimum.

The problem is to predict a human individual's eye color based on data for multilocus genotypes. The results from a study of 300 individuals were conducted.

Within population variance-covariance matricies were computed, and randomly selected individuals were classified based on their genetic distance from the mean of each eye color class (FIG. 16). If one considers light eyes=Blue, Green, and Hazel, and Dark eyes=Brown and Brown 3 (a dark brown), then the classifier is found to be, on average, 82.2% accurate in classifying an individual into the proper shade of eye color. It so happens that, for this trait and these markers, the quadratic classifier is most appropriate.

TABLE 3

Linear classification matrix for randomly selected individuals of varying eye color. The frequency with which individuals of a given eye color class are classified as belonging to a given eye color class is shown.

|  | Blue | Green | Hazel | Brown3 | Brown |
|---|---|---|---|---|---|
| Blue | 0.4457 | 0.22 | 0.1566 | 0.012 | 0.1566 |
| Green | 0.1818 | 0.5909 | 0.1363 | 0 | 0.09 |
| Hazel | 0.2372 | 0.2203 | 0.40677 | 0.0169 | 0.118 |
| Brown3 | 0.0602 | 0.048 | 0.024 | 0.795 | 0.072 |
| Brown | 0.1176 | 0.098 | 0.137 | 0.176 | 0.4705 |

Quadratic classification Procedure for Human Eye colors. The quadratic discriminant score for the i'th trait value is:

$$D^2_{ij,k} = \ln|S_k| + (Y_{ij-\mu k})' S^{-i}_k (Y_{ij-\mu k}) \text{ for } k=1, 2, \ldots$$
$$,g(\text{eye colors}) \quad (4)$$

Classification is then simply the allocation of the ij'th individual to that trait value for which (4) is minimum.

For the example problem of human eye color, using the 5 optimal haplotype systems, the quadratic classifier results in a more accurate classification matrix than the linear classifier (see Table 4 below). Because the samples have different means and unequal variances, the Quadratic classification procedure is more appropriate for the data that we considered above. Not only are blue-eyed individuals classified as blue-eyed, green-eyed classified as green-eyed, etc., more accurately using the quadratic approach, but the classification of individuals into the proper shade of eye color (Light or Dark) is more accurate as well (see Table 5 below). When accuracy is measured in terms of an individual of a given eye color shade properly classified into that eye color shade, the quadratic method produced a 93% accuracy rate (see Table 6 below).

TABLE 4

Quadratic classification matrix for randomly selected individuals of varying eye color. The frequency with which individuals of a given eye color class are classified as belonging to that a given eye color class is shown.

|        | Blue    | Green   | Hazel  | Brown3 | Brown  |
|--------|---------|---------|--------|--------|--------|
| Blue   | 0.54321 | 0.04819 | 0.3253 | 0.0241 | 0.06   |
| Green  | 0.045   | 0.9545  | 0      | 0      | 0      |
| Hazel  | 0.1525  | 0.0508  | 0.7118 | 0.0169 | 0.0677 |
| Brown3 | 0.036   | 0       | 0.1325 | 0.807  | 0.024  |
| Brown  | 0.098   | 0.0588  | 0.2156 | 0.196  | 0.4313 |

TABLE 5

Accuracy of the quadratic classification method in terms of eye color shade for various eye colors. The eye color shade is shown in Columns 2 and 3. The eye colors are shown in each row.

| Eye Color | Light  | Dark   |
|-----------|--------|--------|
| Blue      | 91.60% | 8.40%  |
| Green     | 100%   | 0%     |
| Hazel     | 91.50% | 8.50%  |
| Brown     | 15.70% | 84.30% |
| Brown3    | 3.60%  | 96.40% |

TABLE 6

Overall accuracy of the quadratic classification method for the two eye color shades.

| SHADE | CORRECT | INCORRECT |
|-------|---------|-----------|
| LIGHT | 94.40%  | 5.60%     |
| DARK  | 90.40%  | 9.60%     |
| TOTAL | 93%     | 7%        |

Thus, methods and apparatus for identifying associations between genetic information and particular genetic traits have been described. A candidate SNP combination is selected from a plurality of candidate SNP combinations for a gene associated with a genetic trait Haplotype data associated with this candidate SNP combination are read for a plurality of individuals and grouped into a positive-responding group and a negative-responding group based on whether predetermined trait criteria for an individual are met. A statistical analysis on the grouped haplotype data is performed to obtain a statistical measurement associated with the candidate SNP combination. The acts of selecting, reading, grouping, and performing are repeated as necessary to identify the candidate SNP combination having the optimal statistical measurement. In one approach, all possible SNP combinations are selected and statistically analyzed. In another approach, a directed search based on results of previous statistical analysis of SNP combinations is performed until the optimal statistical measurement is obtained. In addition, the number of SNP combinations selected and analyzed may be reduced based on a simultaneous testing procedure.

It is to be understood that the above is merely a description of preferred embodiments of the invention and that various changes, alterations, and variations may be made without departing from the true spirit and scope of the invention as set for in the appended claims. None of the terms or phrases in the specification and claims has been given any special particular meaning different from the plain language meaning to those skilled in the art, and therefore the specification is not to be used to define terms in an unduly narrow sense.

What is claimed is:

1. A method of identifying an association between genetic information and a particular genetic trait, the method being carried out by computer program instructions and comprising the acts of:
performing an iterative analytical process on a plurality of single nucleotide polymorphisms (SNPs) for candidate SNP combinations of N SNPs;
the iterative analytical process comprising the acts of:
selecting one candidate SNP combination from the candidate SNP combinations;
reading haplotype data associated with the candidate SNP combination for a plurality of individuals;
grouping the haplotype data of the plurality of individuals into a trait-exhibiting group and a non-exhibiting group based on whether a predetermined trait criteria for an individual is met;
performing a statistical analysis on the grouped haplotype data to obtain a statistical measurement associated with the candidate SNP combination;
repeating the acts of selecting, reading, grouping, and performing as necessary for additional SNP combinations of the candidate SNP combinations in order to identify one or more optimal SNP combinations from the candidate SNP combinations;
reducing a number of candidate SNP combinations of M SNPs of the plurality of SNPs for which to perform the iterative analytical process based on the one or more optimal SNP combinations of N SNPs identified from performing the iterative analytical process on the candidate SNP combinations of N SNPs; and
performing the iterative analytical process on the plurality of SNPs for the reduced number of candidate SNP combinations of M SNPs, wherein M and N are natural numbers and N<M.

2. The method of claim 1, wherein N=3.

3. The method of claim 1, wherein the act of reducing the number of SNP combinations of M SNPs for which to perform the iterative analytical process reduces a computational time in which to perform the iterative analytical process on the SNP combinations of M SNPs.

4. The method of claim 1, wherein the act of reducing the number of SNP combinations of M SNPs for which to perform the iterative analytical process comprises the further act of giving a preference to SNP combinations of M SNPs that incorporate the one or more optimal SNP combinations of N SNPs.

5. The method of claim 1, wherein the act of reducing the number of candidate SNP combinations of M SNPs comprises the further act of reducing the number from all possible combinations of M SNPs.

6. The method of claim 1, wherein the act of repeating as necessary is performed such that all possible SNP combinations of N SNPs are statistically analyzed.

7. The method of claim 1, wherein the act of grouping comprises the further act of grouping based on phenotype data for the plurality of individuals.

8. The method of claim 1, wherein the act of grouping comprises the further act of grouping based on phenotype data that indicate a response or non-response to a particular drug.

9. The method of claim 1, wherein the act of grouping comprises the further act of grouping based on phenotype data that indicate whether a physical trait is exhibited.

10. The method of claim 1, wherein N=2.

11. The method of claim 1, wherein the act of reducing the number of SNP combinations of M SNPs comprises the further act of biasing the selection of SNP combinations of M SNPs for the iterative analytical process based on the one or more optimal SNP combinations of N SNPs identified from performing the iterative analytical process on the SNP combinations of N SNPs.

12. A computer program product for identifying an association between genetic information and a particular genetic trait, the computer program product comprising:
a computer readable medium;
computer program instructions embedded in the computer readable medium;
the computer program instructions being executable to perform the following acts:

performing an iterative analytical process on a plurality of candidate single nucleotide polymorphisms (SNPs) for candidate SNP combinations of N SNPs;

the iterative analytical process comprising the acts of:
- selecting one candidate SNP combination from the candidate SNP combinations;
- reading haplotype data associated with the candidate SNP combination for a plurality of individuals;
- grouping the haplotype data of the plurality of individuals into a trait-exhibiting group and a non-exhibiting group based on whether a predetermined trait criteria for an individual is met;
- performing a statistical analysis on the grouped haplotype data to obtain a statistical measurement associated with the candidate SNP combination;
- repeating the acts of selecting, reading, grouping, and performing as necessary for additional SNP combinations of the candidate SNP combinations in order to identify one or more optimal SNP combinations from the candidate SNP combinations;

reducing a number of candidate SNP combinations of M SNPs of the plurality of SNPs for which to perform the iterative analytical process based on the one or more optimal SNP combinations of N SNPs identified from performing the iterative analytical process on the candidate SNP combinations of N SNPs; and performing the iterative analytical process on the plurality of SNPs for the reduced number of candidate SNP combinations of M SNPs, wherein M and N are natural numbers and N<M.

13. The computer program product of claim 12, wherein the computer instructions are further executable for reducing the number of candidate SNP combinations of M SNPs by reducing the number from all possible combinations of M SNPs.

14. A computer device for developing a genetic classification test, comprising:
- the computer device being adapted to perform an iterative analytical process on a plurality of single nucleotide polymorphisms (SNPs) for candidate SNP combinations of N SNPs for a gene associated with a genetic trait;
- the computer device being adapted to perform the iterative analytical process with use of:
  - a data selector which selects one candidate SNP combination from the candidate SNP combinations;
  - a data reader which reads haplotype data associated with the candidate SNP combination for a plurality of individuals;
  - a data grouper which groups the haplotype data of the plurality of individuals into a trait-exhibiting group and a non-exhibiting group based on whether a predetermined trait criteria for an individual is met;
  - a statistical analysis processor which performs a statistical analysis on the grouped haplotype data to obtain a statistical measurement associated with the candidate SNP combination;
  - a decision component which causes the selecting, reading, grouping, and performing to be repeated as necessary in the iterative analytical process for additional candidate SNP combinations of the candidate SNP combinations, such that one or more optimal SNP combinations are identified from the candidate SNP combinations;
- the computer device having a processing component which reduces a number of candidate SNP combinations of M SNPs of the plurality of SNPs for which to perform the iterative analytical process based on the one or more optimal SNP combinations of N SNPs identified from performing the iterative analytical process on the candidate SNP combinations of N SNPs; and
- the computer device being further adapted to perform the iterative analytical process on the plurality of SNPs for the reduced number of candidate SNP combinations of M SNPs, wherein M and N are natural numbers and N<M.

15. The computer device of claim 14, wherein the processing component is configured to perform a directed search of SNP combinations of M SNPs based on the one or more optimal SNP combinations of N SNPs.

16. The computer device of claim 14, wherein the processing component reduces the number of candidate SNP combinations of M SNPs from the number of all possible combinations of M SNPs.

17. The computer device of claim 14, further comprising:
a statistical modeling processor which statistically models data associated with the one or more optimal SNP combinations.

18. The computer device of claim 17, wherein the genetic classification test is developed based on results of the statistical modeling processor.

19. A method of identifying an association between genetic information and a particular genetic trait, the method being carried out by computer program instructions and comprising the acts of:
- performing an iterative analytical process on a plurality of single nucleotide polymorphisms (SNPs) for candidate SNP combinations of N SNPs;
- the iterative analytical process comprising the acts of:
  - selecting one candidate SNP combination from the candidate SNP combinations;
  - reading haplotype data associated with the candidate SNP combination for a plurality of individuals;
  - grouping the haplotype data of the plurality of individuals into a trait-exhibiting group and a non-exhibiting group based on whether a predetermined trait criteria for an individual is met;
  - performing a statistical analysis on the grouped haplotype data to obtain a statistical measurement associated with the candidate SNP combination;
  - repeating the acts of selecting, reading, grouping, and performing as necessary for additional SNP combinations of the candidate SNP combinations in order to identify one or more optimal SNP combinations from the candidate SNP combinations;
- reducing a number of candidate SNP combinations of M SNPs of the plurality of SNPs for which to perform the iterative analytical process based on the one or more optimal SNP combinations of N SNPs identified from performing the iterative analytical process on the candidate SNP combinations of N SNPs; and
- performing the iterative analytical process on the plurality of SNPs for the reduced number of candidate SNP combinations of M SNPs, wherein M and N are natural numbers and N<M.

20. The method of claim 19, wherein the act of reducing comprises the further act of reducing the number of SNP combinations of M SNPs based on a simultaneous testing procedure.

21. A computer program product comprising a computer readable medium and computer program instructions stored in the computer readable medium which executes the method of claim 19.

* * * * *

UNITED STATES PATENT AND TRADEMARK OFFICE
CERTIFICATE OF CORRECTION

PATENT NO. : 7,107,155 B2  
APPLICATION NO. : 10/120804  
DATED : September 12, 2006  
INVENTOR(S) : Frudakis It is certified that error appears in the above-identified patent and that said Letters Patent is hereby corrected as shown below:

Col. 4 Line 35: AGGC, AGCT, AGTC, AGTT, AACC, AACT, AATC, AATT

Changed to

Col. 4: Line 35: AGCC, AGCT, AGTC, AGTT, AACC, AACT, AATC, AATT

Signed and Sealed this

Fifth Day of December, 2006

JON W. DUDAS  
*Director of the United States Patent and Trademark Office*

SEQUENCE LISTING

<160> NUMBER OF SEQ ID NOS: 12

<210> SEQ ID NO 1
<211> LENGTH: 14
<212> TYPE: DNA
<213> ORGANISM: Homo Sapiens

<400> SEQUENCE: 1
agtctgcccc atgg                                                     14

<210> SEQ ID NO 2
<211> LENGTH: 14
<212> TYPE: DNA
<213> ORGANISM: Homo Sapiens

<400> SEQUENCE: 2
actctgccca atgg                                                     14

```
<210> SEQ ID NO 3
<211> LENGTH: 10
<212> TYPE: DNA
<213> ORGANISM: Homo Sapiens

<400> SEQUENCE: 3
gcatgacttg                                                          10

<210> SEQ ID NO 4
<211> LENGTH: 10
<212> TYPE: DNA
<213> ORGANISM: Homo Sapiens

<400> SEQUENCE: 4
ccttagcggg                                                          10

<210> SEQ ID NO 5
<211> LENGTH: 10
<212> TYPE: DNA
<213> ORGANISM: Homo Sapiens

<400> SEQUENCE: 5
ggatgacttg                                                          10

<210> SEQ ID NO 6
<211> LENGTH: 10
<212> TYPE: DNA
<213> ORGANISM: Homo Sapiens

<400> SEQUENCE: 6
cgttagcggg                                                          10

<210> SEQ ID NO 7
<211> LENGTH: 10
<212> TYPE: DNA
<213> ORGANISM: Homo Sapiens

<400> SEQUENCE: 7
gcatgacttg                                                          10

<210> SEQ ID NO 8
<211> LENGTH: 10
<212> TYPE: DNA
<213> ORGANISM: Homo Sapiens

<400> SEQUENCE: 8
ccttagcggg                                                          10

<210> SEQ ID NO 9
<211> LENGTH: 10
<212> TYPE: DNA
<213> ORGANISM: Homo Sapiens

<400> SEQUENCE: 9
ggatgacttg                                                          10

<210> SEQ ID NO 10
<211> LENGTH: 10
<212> TYPE: DNA
<213> ORGANISM: Homo Sapiens

<400> SEQUENCE: 10
```

<210> SEQ ID NO 11
<211> LENGTH: 1395
<212> TYPE: DNA
<213> ORGANISM: Homo Sapiens

<400> SEQUENCE: 11

| | | | | | |
|---|---|---|---|---|---|
| ctgggactag | agtctgcaca | tttaactatg | ggtggtgttg | tgttttgtgc | ttagatggtc | 60 |
| cctatcattg | cccagtatgg | agatgtgttg | gtgagaaatc | tgaggcggga | agcagagaca | 120 |
| ggcaagcctg | tcaccttgaa | agagtaagta | aagcgcagc | catggggttc | tgagctgtca | 180 |
| tgaacccctc | cagctgcctg | ccatggagct | gatattcctg | ctgttgggtt | attccagtga | 240 |
| ccagacaaaa | ggagggctgt | ggtaatgcaa | cttcaatggg | tctcccaaga | tggggcagct | 300 |
| ccgatgagga | ggtggggcag | ctggaggaaa | aggatcttct | ccctgtgca | caggggccag | 360 |
| ggtttacata | tccattaaat | tgtcaccttg | gatattctag | aagactaaat | atatccttta | 420 |
| gggggaaaaa | gtgtgattgt | accaaagttt | taagcatgga | gtgtatggga | tggtggaagg | 480 |
| ggaaggcact | tggtatctgt | tggttggcag | tgagtaggtt | gggagagtta | taatggagaa | 540 |
| cttagaataa | ctttgatcat | ttcatgtttt | tttctgagga | tatcagtaga | atactaaata | 600 |
| ttaaaattcc | taccatttct | ttttcctcca | gtctcaaaga | gagagggtgg | taaaaacact | 660 |
| ataggtaggg | caagcctatt | atttgctatc | tacacttatg | cagtaaaaac | aggtgtaatc | 720 |
| tgagtttgtc | ctgggcagac | cagggatatg | tggtcactca | ctatagaaat | ttccaaatca | 780 |
| aattttgaga | gatttttttt | taaccaggac | attattggtc | attatatttt | acaaaaataa | 840 |
| gtatagagaa | taaggatgat | atttctagga | gctcagaaca | gggtactgtt | gctttgtaaa | 900 |
| gtgctgaaga | ggaatcggct | ctgggcatag | agtctgcagt | caggcaatat | cacctgtctt | 960 |
| gagcccctta | ggaagagtta | attattctac | tcttgttctg | ctgaagcaca | gtgcttaccc | 1020 |
| atcttgtatc | atccacaatc | aatacatgct | actgtagttg | tctgatagtg | ggtctctgtc | 1080 |
| ttcctatgat | gggcgccttg | atctcagagg | taggtctaat | tcagttcagt | gtctccatca | 1140 |
| cacccagcgt | agggccagct | gcatcactgg | cacctgataa | caccttctga | tggagtgtga | 1200 |
| tagaaggtga | tctagtagat | ctgaaagtct | gtggctgttt | gtctgtccttg | actggacatg | 1260 |
| tgggtttcct | gttgcatgca | tagaggaagg | akggtaaaaa | ggtgctgatt | ttaatttttcc | 1320 |
| acatctttct | ccactcagcg | tctttggggc | ctacagcatg | gatgtgatca | ctagcacatc | 1380 |
| atttggagtg | aacat | | | | | 1395 |

<210> SEQ ID NO 12
<211> LENGTH: 1190
<212> TYPE: DNA
<213> ORGANISM: Homo Sapiens

<400> SEQUENCE: 12

| | | | | | |
|---|---|---|---|---|---|
| ctctcaacaa | tccacaagac | ccctttgtgg | aaaacaccaa | gaagctttta | agatttgatt | 60 |
| ttttggatcc | attctttctc | tcaataagta | tgtggactac | tatttccttt | aatttatctt | 120 |
| kctctcttaa | aaataactgc | tttattgaga | tataaatcac | catgtaattc | akccacttwa | 180 |
| aatatacagt | tcagtgattt | gtagtacatt | tgaagatatg | tgtgaccatc | atcattttaa | 240 |
| actttaaaac | ttttttttgtc | aatctagaga | cctcatacat | ttttagctat | cagcccctg | 300 |
| tcacaaaccc | tgtcatcata | tgcaaccact | aatcaacttt | ctgcttctat | ggatttgcct | 360 |
| attctggaca | cttcatagaa | atgatattaa | ttcatcaggg | ttttttattc | tctagttcat | 420 |

```
tactatgttg tggcatgaac atagattact gatttgtgat ttttttgttc ctctaaattt        480
agacattaca gctgtaactt tccctctgag cacttccttt gctaaatccc atgagattgt        540
ggcctatcac atcttagttt tgttcacctc aaaacagttt ctatttgccc tttgggtttc        600
tactttgact cattgggtac ttaaatgttt attatttaac ttccacatat gtgtgagttt        660
ctcaattttc tttcccttat tgattttatc tttattccat gataggtgac agagatatgc        720
tgtgttattt ctatcttgac tacctactat ttcttgaaca gcaagattaa ttttgagctt        780
cagattatga tttgggttat tctaggagac tgtagtccaa tagataaagg caaagagatt        840
agggcattga attttgttcc ttttatcctt caaaagatgc acaagggct gctgatctca         900 ctgctgtagc ggtgctcctt atgcatagac ctgcccttgc tcagccactg gcctgaaaga        960
ggggcaaaag tcatagaagg aatggcttcc agttgagaac cttgatgtct tttactcttc       1020
tggttggtag agaaaactag aattgctcca ggtaaatttt gcacattcac aatgaatttc       1080
tttttctgtt tttgttttgt ttttcctaca gcagtctttc cattcctcat cccaattctt       1140
gaagtattaa atatctgtgt gtttccaaga gaagttacaa attttttaag                  1190
```